(12) United States Patent
Matheny

(10) Patent No.: US 12,053,372 B2
(45) Date of Patent: *Aug. 6, 2024

(54) PROSTHETIC HEART VALVES

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 843 days.

This patent is subject to a terminal disclaimer.

(21) Appl. No.: 17/177,359

(22) Filed: Feb. 17, 2021

(65) Prior Publication Data

US 2021/0169643 A1    Jun. 10, 2021

Related U.S. Application Data

(63) Continuation-in-part of application No. 16/129,968, filed on Sep. 13, 2018, now Pat. No. 10,952,843, and
(Continued)

(51) Int. Cl.
*A61F 2/24* (2006.01)
*A61L 27/36* (2006.01)
(Continued)

(52) U.S. Cl.
CPC ........ *A61F 2/2412* (2013.01); *A61L 27/3604* (2013.01); *A61L 27/3629* (2013.01); *A61L 27/3633* (2013.01); *A61L 27/3826* (2013.01); *A61L 27/3834* (2013.01); *A61L 27/50* (2013.01); *A61F 2/2409* (2013.01); *A61F 2/2457* (2013.01); *A61F 2/246* (2013.01); *A61F 2210/0014* (2013.01); *A61F 2220/0075* (2013.01); *A61F 2230/0067* (2013.01);
(Continued)

(58) Field of Classification Search
CPC .................. A61F 2/2412; A61F 2/2457; A61F 2230/0067; A61L 27/3629; A61L 27/3633; A61L 27/3873
See application file for complete search history.

(56) References Cited

U.S. PATENT DOCUMENTS 6,117,979 A    9/2000  Hendriks et al.
2009/0324674 A1  12/2009  Burne et al.
(Continued)

*Primary Examiner* — Suba Ganesan
(74) *Attorney, Agent, or Firm* — Thomas | Horstemeyer, LLP

(57) ABSTRACT

Prosthetic heart valves having a conical shaped base valve structure formed from collagenous mammalian tissue. The base valve structure includes a plurality of elongated ribbon members that are positioned proximate each other in a joined relationship, wherein the elongated ribbon members are positioned adjacent each other and form a plurality of fluid flow modulating regions that open when fluid into and through the base valve structure exhibits a positive pressure relative to the exterior pressure, i.e., a positive pressure differential, wherein the fluid is allowed to be transmitted out of the base valve structure, and transition to a closed configuration when the pressure differential between the interior valve pressure and exterior pressure reduces, wherein the fluid is restricted from flowing out of the base valve structure.

8 Claims, 17 Drawing Sheets

Related U.S. Application Data a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61L 27/38* (2006.01)
*A61L 27/50* (2006.01)

(52) U.S. Cl.
CPC ......... *A61L 27/367* (2013.01); *A61L 27/3873* (2013.01); *A61L 2300/104* (2013.01); *A61L 2300/404* (2013.01); *A61L 2300/406* (2013.01); *A61L 2300/41* (2013.01); *A61L 2300/414* (2013.01); *A61L 2300/416* (2013.01); *A61L 2300/42* (2013.01); *A61L 2300/606* (2013.01); *A61L 2430/20* (2013.01)

(56) References Cited

U.S. PATENT DOCUMENTS

| | | | |
|---|---|---|---|
| 2017/0014183 A1 | 1/2017 | Gifford, III et al. | |
| 2018/0153686 A1 | 6/2018 | Matheny | |
| 2019/0008634 A1* | 1/2019 | Matheny | A61L 27/50 |
| 2020/0368178 A1 | 11/2020 | Naso et al. | |

* cited by examiner

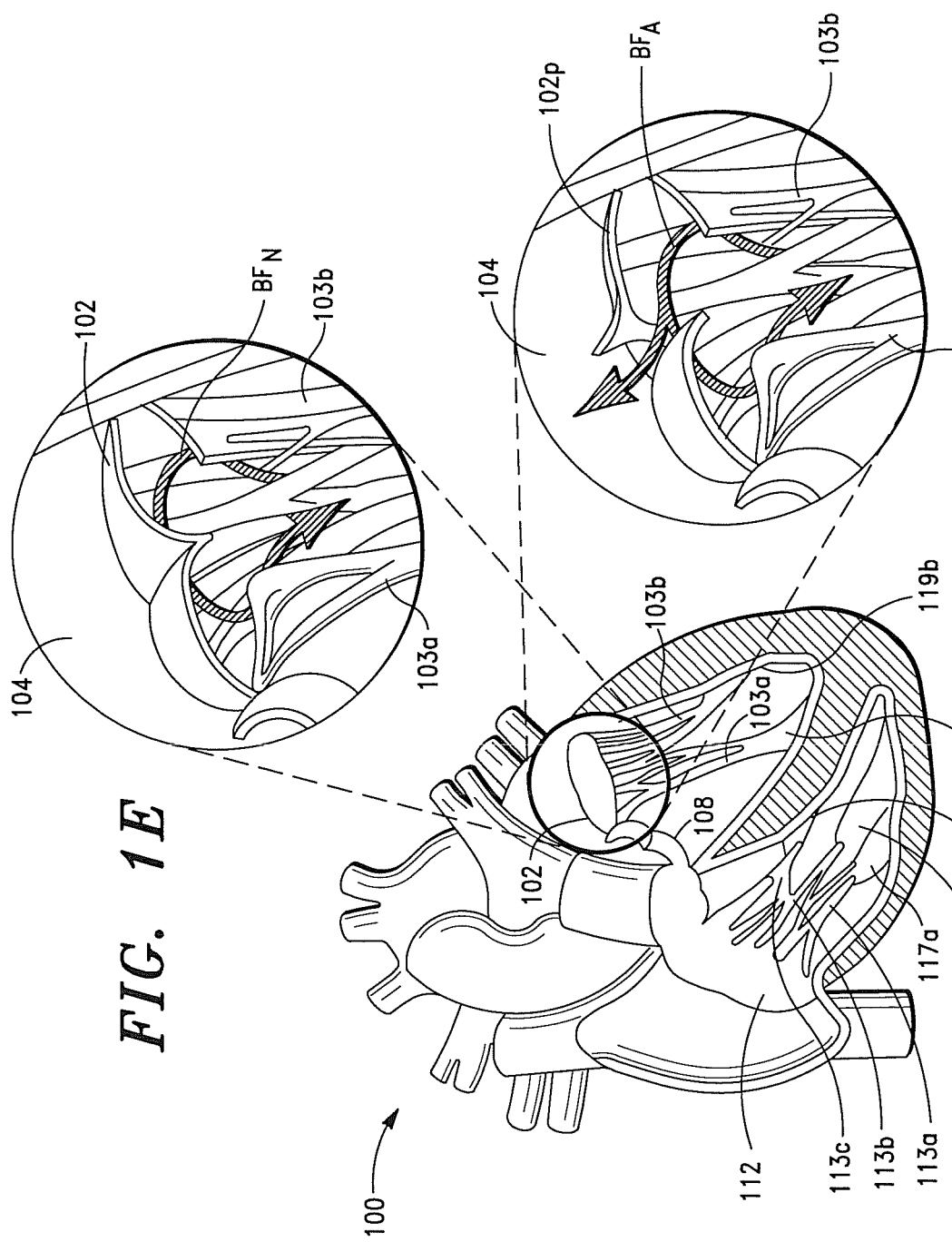

Nominal Mitral Valve Measurements

Mitral Valve Annulus

| Anteroposterior diameter | 30.8 ± 4.5mm |
|---|---|
| Commissural diameter | 35.1 ± 4.9mm |
| Annular perimeter | 120.55 ± 8.5mm |
| Height | 4.3 ± 2.1mm |

Papillary Muscles

| Annulus to AL papillary distance | 21.0 ± 5.8mm – 37.2mm ± 4.5mm |
|---|---|
| Annulus to PM papillary distance | 22.3 ± 5.6mm – 38.7mm ± 3.2mm |

PROSTHETIC HEART VALVES

CROSS-REFERENCE TO RELATED APPLICATIONS

This application is a continuation-in-part of U.S. application Ser. No. 16/129,968, filed on Sep. 13, 2018, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic heart valves for replacing diseased or defective heart valves. More particularly, the present invention relates to improved prosthetic heart valves and methods for replacing native heart valves with same.

BACKGROUND OF THE INVENTION

As is well known in the art, the human heart has four heart valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendineae 113a, 113b, 113c to the tricuspid valve 112. The anterior and posterior papillary muscles 119a, 119b of the left ventricle 106 attach via chordae tendineae 103a, 103b to the mitral valve 102 (see also FIG. 1E).

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordae or several disease states. Stenosis and insufficiency can also occur concomitantly in the same valve or in different valves.

Both of the noted valve abnormalities can adversely affect organ function and result in heart failure. By way of example, referring first to FIG. 1E, there is shown normal blood flow (denoted "BFN") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e., "vegetation") on the valve leaflets. The vegetation can, and in many instances will, flake off (i.e., "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e., a prosthetic valve.

Various prosthetic heart valves have thus been developed for replacement of native diseased or defective heart valves. The selection of a particular type of replacement valve depends on many factors, such as the location of the diseased or defective native valve, the age and other specifics of the recipient of the replacement heart valve, and the surgeon's experiences and preferences.

Commonly used replacement heart valves are typically classified in the following three groups: (i) mechanical valves, (ii) allograft tissue valves, and (iii) xenograft tissue valves. Each of the noted valves and disadvantages associated with same are discussed in detail below.

Mechanical Heart Valves

As is well known in the art, mechanical heart valves, such as caged-ball valves, bi-leaflet valves, and tilting disk valves, typically comprise various metal and polymeric components, which can, and in most instances will, induce an adverse inflammatory response when implanted in a patient or subject.

A further disadvantage associated with mechanical heart valves is that such valves also have a propensity to cause the formation of blood clots after implantation in a patient. If such blood clots form on the mechanical valve, they can preclude the valve from opening or closing correctly or, more importantly, can disengage from the valve and embolize to the brain, causing an embolic stroke. Thus, recipients of a mechanical heart valve are typically required to take systemic anticoagulant drugs for the rest of their lives. In addition to being expensive, these anticoagulant drugs can themselves be dangerous in that they can cause abnormal bleeding in the recipient or patient that can lead to a hemorrhagic stroke.

A further disadvantage associated with mechanical heart valves is that such valves often have large and cumbersome skirt attachments that partially extend into the left atrium and the left ventricle when implanted in a mitral valve region. The skirt attachment can, and often will, impair aortic valve function by obstructing the outflow tract of the aortic valve and preventing the leaflets of the adjacent aortic valve from coapting. In some instances, mechanical heart valves can reduce the outflow blood rate of the aortic valve by up to 50%.

The risks and complications associated with impaired aortic valve function typically include left ventricular hypertrophy with fibrosis, systolic dysfunction (a decrease in the ejection fraction), diastolic dysfunction (elevated filling pressure of the LV), and in severe cases, congestive heart failure.

Further, mechanical heart valves with and without the skirt attachments are notoriously difficult to implant and often require large and cumbersome catheter assemblies for percutaneous or transapical implantation. These large catheter assemblies are excessively difficult to operate during a percutaneous or transapical implantation procedure.

Allograft Tissue Valves

As is also well known in the art, allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major drawback associated with allograft tissue valves is that such valves are not available in sufficient numbers to satisfy the needs of all patients who need new heart valves.

A further major drawback associated with allograft tissue valves is that recipients of allograft tissue valves, i.e., patients, are typically required to take systemic antirejection and/or immunosuppressive drugs for a predetermined period of time and, in some instances, for a lifetime. Although antirejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Xenograft Tissue Valves

As is additionally well known in the art, xenograft tissue valves are formed from non-human tissue sources, such as cows or pigs. Xenograft tissue valves are similarly less likely to cause blood clot formation than comparable mechanical valves. However, there are also several drawbacks and disadvantages associated with most conventional allograft tissue valves.

A major drawback associated with conventional xenograft tissue valves is that such valves often comprise glutaraldehyde processed tissue and, hence, are prone to calcification and lack the long-term durability of mechanical valves.

More recently, remodelable xenograft tissue valves comprising decellularized extracellular matrix (ECM) have been developed and employed to replace native diseased or defective heart valves. Such valves are not prone to calcification and, as set forth in Applicant's U.S. Pat. Nos. 9,308,084, 9,011,526, 8,709,076 and Co-pending U.S. application Ser. No. 16/129,968, which are expressly incorporated by reference herein in their entirety, have the capacity to remodel, i.e., form valve structures similar to native valve structures when implanted in a patient, and induce remodeling of native cardiovascular tissue and regeneration of new cardiovascular tissue when implanted in a patient.

Although most remodelable xenograft ECM tissue valves substantially reduce and, in most instances, eliminate the major disadvantages and drawbacks associated with mechanical valves, allograft tissue valves, and conventional xenograft tissue valves, a remaining drawback associated with most xenograft tissue valves (non-remodelable and remodelable) is that, by virtue of their shape and required attachment to a valve annulus region; particularly, a mitral valve annulus region, and a cardiovascular structure, such as the papillary muscles (denoted "$119a$" and "$119b$" in FIG. 1C), is disruption of blood flow out of the left ventricle (denoted "$BF_o$" in FIG. 1H) and into and, hence, through the aortic valve 108.

A further major drawback is that, when many xenograft tissue valves (non-remodelable and remodelable) are attached to a mitral valve annulus, a higher valvular pressure gradient is generated across the mitral valve annulus region between the left atrium and left ventricle, which significantly disrupts blood flow out of the left atrium and into the left ventricle during ventricular diastole/atrial systole.

An additional drawback associated with many xenograft tissue valves (remodelable and non-remodelable), mechanical valves and allograft tissue valves is that, by virtue of their shape, such valves have a limited leaflet coaptation surface area, which can, and often will delay ventricular filling during ventricular diastole/atrial systole.

The noted drawbacks and disadvantages associated with xenograft tissue valves (remodelable and non-remodelable), mechanical valves and allograft tissue valves has, however, recently been effectively addressed via Applicant's development of conical shaped prosthetic valves. Illustrative conical shaped prosthetic valves are disclosed in Applicant's issued U.S. Pat. Nos. 10,052,409, 10,188,509, 10,188,510 and 10,188,513, and Co-pending U.S. application Ser. Nos. 16/129,968, 16/440,504 and 16/553,499.

The conical shaped prosthetic valves developed by Applicant and disclosed in the noted patents and applications do, however, primarily comprise "remodelable" xenograft tissue, whereby the valves have the capacity to remodel and form valve structures similar to native valve structures, and induce remodeling of native cardiovascular tissue and regeneration of new cardiovascular tissue when implanted in a patient, and polymeric compositions.

There thus remains a need to provide "non-remodelable" prosthetic xenograft tissue valves having a structure that substantially reduces disruption of blood flow out of the left ventricle and into and, hence, through the aortic valve, when implanted in a patient.

There also remains a need for prosthetic xenograft valves with improved blood flow modulation and characteristics.

There additionally remains a need for improved prosthetic xenograft valves with minimal in vivo calcification and cytotoxicity.

It is therefore an object of the present invention to provide "non-remodelable" prosthetic xenograft valves having a structure that substantially reduces disruption of blood flow out of the left ventricle and into and, hence, through the aortic valve, when implanted in a patient.

It is another object of the present invention to provide prosthetic xenograft valves with optimal blood flow modulation and characteristics.

It is another object of the present invention to provide improved prosthetic xenograft valves with minimal in vivo calcification and cytotoxicity.

It is another object of the present invention to provide "non-remodelable" prosthetic xenograft valves having the capacity to deliver biologically active agents, such as growth factors, and pharmacological agents, such as anti-inflammatories, to cardiovascular tissue, when disposed proximate thereto.

It is yet another object of the present invention to provide improved methods for replacing diseased or defective native heart valves with prosthetic xenograft valves.

SUMMARY OF THE INVENTION

The present invention is directed to prosthetic heart valves that can be readily employed to replace diseased or defective native heart valves.

In a preferred embodiment of the invention, the prosthetic valves comprise continuous conical shaped structural members having a plurality of flow modulation means.

In some embodiments of the invention, the conical shaped structural members comprise conical shaped sheet structures.

In the noted embodiments, the flow modulation means comprise linear interstices.

In some embodiments of the invention, the conical shaped structural members comprise conical shaped ribbon structures having a plurality of elongated ribbon members.

In a preferred embodiment of the invention, the edge regions of the elongated ribbon members are positioned proximate each other and form the fluid flow modulating means.

In a preferred embodiment of the invention, the distal ends of the elongated ribbon members are in a joined relationship, wherein fluid flow through the joined distal ends of the elongated ribbon members is restricted.

In a preferred embodiment of the invention, the prosthetic valves comprise collagenous mammalian tissue derived from a mammalian tissue source.

In some embodiments of the invention, the collagenous mammalian tissue comprises pericardium tissue.

In some embodiments of the invention, the pericardium tissue comprises crosslinked pericardium tissue.

In some embodiments of the invention, the collagenous mammalian tissue comprises an exogenously added biologically active agent, such as a growth factor of cell.

In some embodiments of the invention, the collagenous mammalian tissue comprises a pharmacological agent (or composition), i.e., an agent or composition that is capable of producing a desired biological effect in vivo, e.g., stimulation or suppression of apoptosis, stimulation or suppression of an immune response, etc.

The present invention is also directed to replacing diseased or defective heart valves with the aforedescribed prosthetic valves of the invention.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

DETAILED DESCRIPTION OF THE PREFERRED EMBODIMENT

Figure 1A:
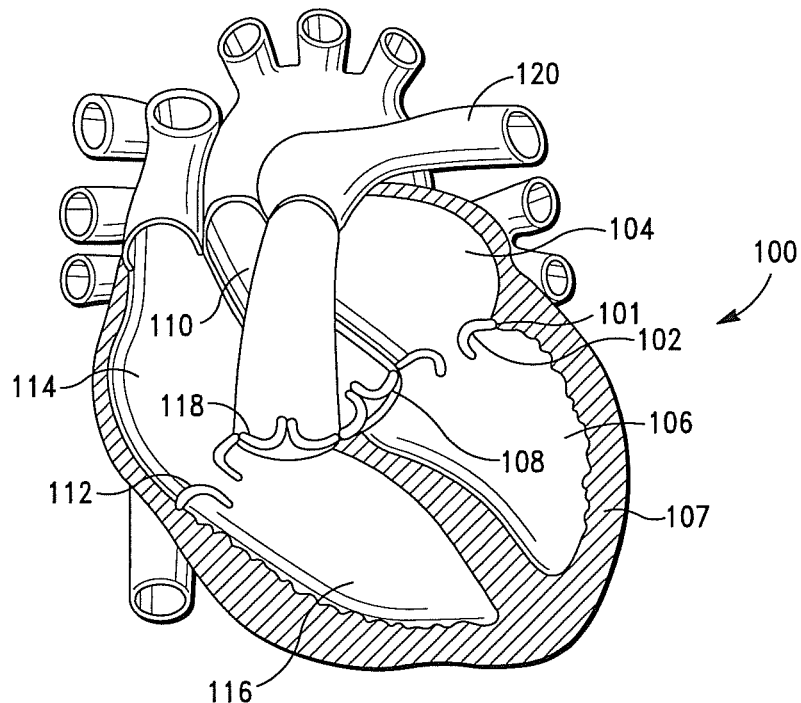

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein are hereby incorporated by reference in their entirety.

As used in this specification and the appended claims, the singular forms "a, "an" and "the" include plural referents unless the content clearly dictates otherwise.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means ECM that has a reduced content of cells.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM can also comprise collagen from mammalian sources.

The terms "heart tissue" and "cardiac tissue" are used collectively herein, and mean and include, without limitation, mammalian tissue derived from any cardiovascular structure including, without limitation, pericardial tissue, myocardial tissue, vascular tissue and the like.

The terms "collagenous mammalian tissue" and "collagenous tissue" are used collectively herein, and mean and include, without limitation, tissue that is also derived from a mammalian tissue source.

According to the invention, the collagenous mammalian tissue can similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

The collagenous mammalian tissue can also be derived from a mammalian tissue source that is devoid of xenogeneic antigens, including, without limitation, collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetylneuraminic acid hydroxylase, swine leukocyte antigen class I and porcine endogenous retrovirus polymerase (referred to herein as "immune privileged collagenous mammalian tissue").

The term "genetically modified organism", as used herein means and includes any living organism that has at least one gene modified by artificial means, e.g., gene editing.

The term "immune privileged collagenous mammalian tissue", as used herein means and includes xenogeneic collagenous mammalian tissue that can be disposed proximate mammalian tissue with a minimal or virtually absent adverse immune response; particularly, an adverse immune response associated with xenogeneic tissue graft rejection.

According to the invention, the term "mammalian" means and includes, without limitation, warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "crosslinked collagenous mammalian tissue", as used herein, means and includes mammalian tissue that exhibits at least 25% chemical bonding of adjacent chains of molecules, i.e., collagen fibrils, which comprise the collagenous mammalian tissue.

The term "polymer", as used herein means and includes, without limitation, polyurethane urea, porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™) and polyethylene terephthalate (Dacron™).

The term "natural polymer", as used herein means and includes, without limitation, polysaccharides (e.g., starch and cellulose), proteins (e.g., gelatin, casein, silk, wool, etc.), and polyesters (e.g., polyhydroxyalkanoates).

The term "biologically active agent", as used herein, means and includes an agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β) and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes an exosome and/or microsome.

The terms "exosome" and "microsome" as used herein mean and include a lipid bilayer structure that contains or encapsulates a biologically active agent and/or pharmacological agent, including, without limitation, a growth factor, e.g., TGF-β, TGF-α, VEGF and insulin-like growth factor (IGF-I), a cytokine, e.g., interleukin-10 (IL-10), a transcription factor and microRNA (miRNA).

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the Class I-Class V antiarrhythmic agents disclosed in Applicant's U.S. Pat. Nos. 9,119,841, 10,188,509, 10,188,510 and 10,143,778, and Co-pending application Ser. Nos. 16/129,968 and 16/990, 236, including, without limitation, (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the antibiotics disclosed in Applicant's U.S. Pat. Nos. 9,119,841, 10,188,509, 10,188,510 and 10,143,778, and Co-pending application Ser. Nos. 16/129,968 and 16/990,236, including, without limitation, aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

The terms "anti-inflammatory" and "anti-inflammatory agent" thus include the anti-inflammatories disclosed in Applicant's U.S. Pat. Nos. 9,119,841, 10,188,509, 10,188, 510 and 10,143,778, and Co-pending application Ser. Nos. 16/129,968 and 16/990,236, including, without limitation, desoximetasone, dexamethasone dipropionate, cloticasone propionate, diftalone, fluorometholone acetate, fluquazone, meseclazone, mesterolone, methandrostenolone, methenolone, methenolone acetate, methylprednisolone suleptanate, halopredone acetate, alclometasone dipropionate, apazone, balsalazide disodium, cintazone cormethasone acetate, cortodoxone, diflorasone diacetate, diflumidone sodium, endrysone, fenpipalone, flazalone, fluretofen, fluticasone propionate, isoflupredone acetate, nabumetone, nandrolone, nimazone, oxyphenbutazone, oxymetholone, phenbutazone, pirfenidone, prifelone, proquazone, rimexolone, seclazone, tebufelone and testosterone.

The terms "pharmacological agent", "active agent" and "drug" also mean and include the statins, i.e., HMG-CoA reductase inhibitors, disclosed in Applicant's U.S. Pat. Nos. 9,119,841, 10,188,509, 10,188,510 and 10,143,778, and Co-pending application Ser. Nos. 16/129,968 and 16/990, 236, including, without limitation, atorvastatin, cerivastatin, fluvastatin and lovastatin.

The terms "pharmacological agent", "active agent", "drug" and "active agent formulation" further mean and include the anti-proliferative agents disclosed in Applicant's U.S. Pat. Nos. 9,119,841, 10,188,509, 10,188,510 and 10,143,778, and Co-pending application Ser. Nos. 16/129, 968 and 16/990,236, including, without limitation, paclitaxel, sirolimus and derivatives thereof, including everolimus.

The term "pharmacological composition", as used herein, means and includes a composition comprising a "pharmacological agent" and/or any additional agent or component identified herein.

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The term "comprise" and variations of the term, such as "comprising" and "comprises," as used in connection with the a prosthetic valve composition and/or mammalian tissue, also means a composition and/or mammalian tissue employed to form a prosthetic valve structure, such as a sheet member, and, hence, a prosthetic valve of the invention.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to improved prosthetic valves and methods for replacing diseased or defective native heart valves with same.

Although the prosthetic valves of the invention are described in connection with prosthetic mitral valves and the replacement of native mitral valves therewith, it is to be understood that the prosthetic valves of the invention are not limited to prosthetic mitral valves and the replacement of native mitral valves therewith. Indeed, the prosthetic valves of the invention can also be readily employed to replace other cardiovascular valves, including tricuspid and venous valves.

As indicated above, in a preferred embodiment, the prosthetic valves of the invention comprise continuous conical shaped structural members having a plurality of flow modulation means.

In some embodiments of the invention, the prosthetic valves comprise conical shaped sheet structures, such as the conical shaped valves disclosed in Applicant's U.S. Pat. Nos. 10,188,509, 10,188,510 and 10,188,513, which are incorporated by reference herein in their entirety.

In some embodiments of the invention, the sheet structures comprise seamless sheet structures, such as the seamless conical shaped valves disclosed in Applicant's U.S. application Ser. Nos. 16/440,504 and 16/553,499, which are also incorporated by reference herein in their entirety.

In the noted sheet structure embodiments, the flow modulation means comprise linear interstices.

In some embodiments of the invention, the conical shaped sheet structures comprise conical shaped ribbon structures having a plurality of elongated ribbon members.

In a preferred embodiment of the invention, the edge regions of the elongated ribbon members are positioned proximate each other and form the fluid flow modulating means.

In a preferred embodiment of the invention, the distal ends of the elongated ribbon members are in a joined relationship, wherein fluid flow through the joined distal ends of the elongated ribbon members is restricted.

In some embodiments of the invention, the proximal ends of the conical shaped prosthetic valves of the invention comprise an annular ring that is designed and configured to securely engage the prosthetic valves to a valve annulus (and, hence, cardiovascular tissue associated therewith).

In some embodiments of the invention, the annular ring comprises at least one anchoring mechanism that is configured to position the prosthetic valves of the invention proximate a valve annulus and maintain contact therewith for a pre-determined anchor support time period.

According to the invention, the anchoring mechanisms can comprise various forms and materials, such as the anchoring mechanisms disclosed in U.S. Pat. No. 9,044,319, which is incorporated by reference herein in its entirety.

According to the invention, the conical shaped prosthetic tissue valves and/or annular ring and/or structural ring can comprise various biocompatible materials and compositions formed therefrom.

Figure 9A:
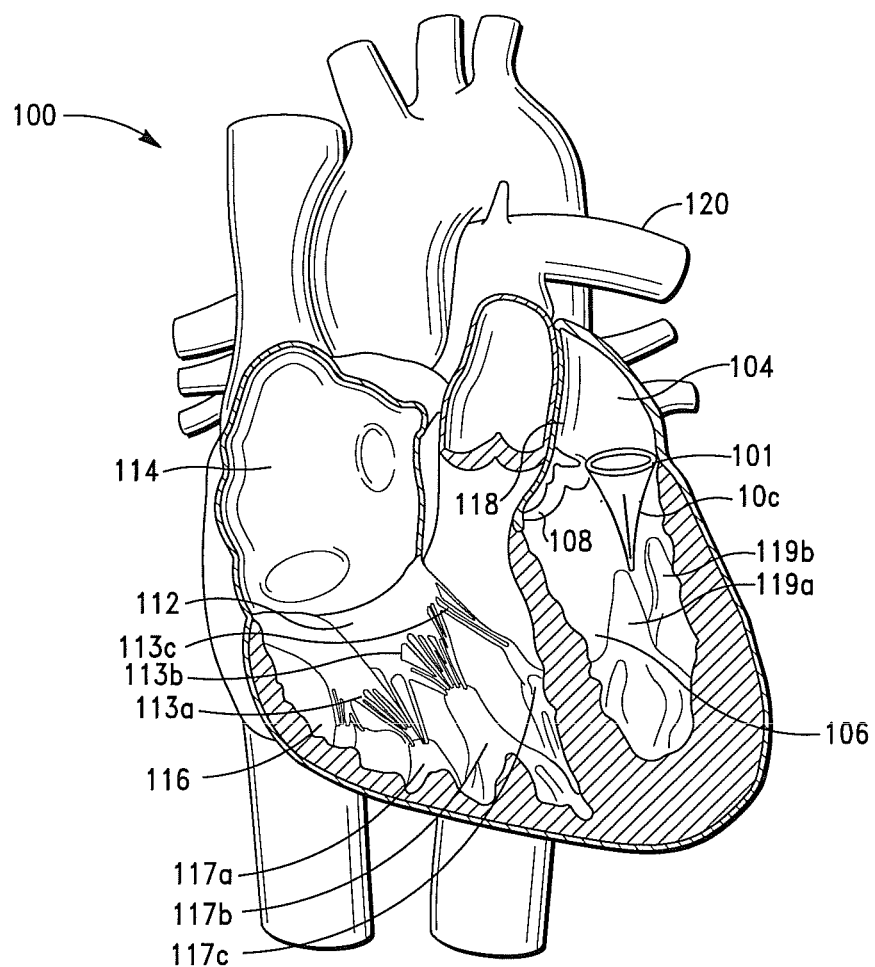
FIG. 9A is an illustration of the prosthetic "sheet structure" valve shown in FIG. 6 secured to a mitral valve annulus region, in accordance with the invention.
Figure 10A:
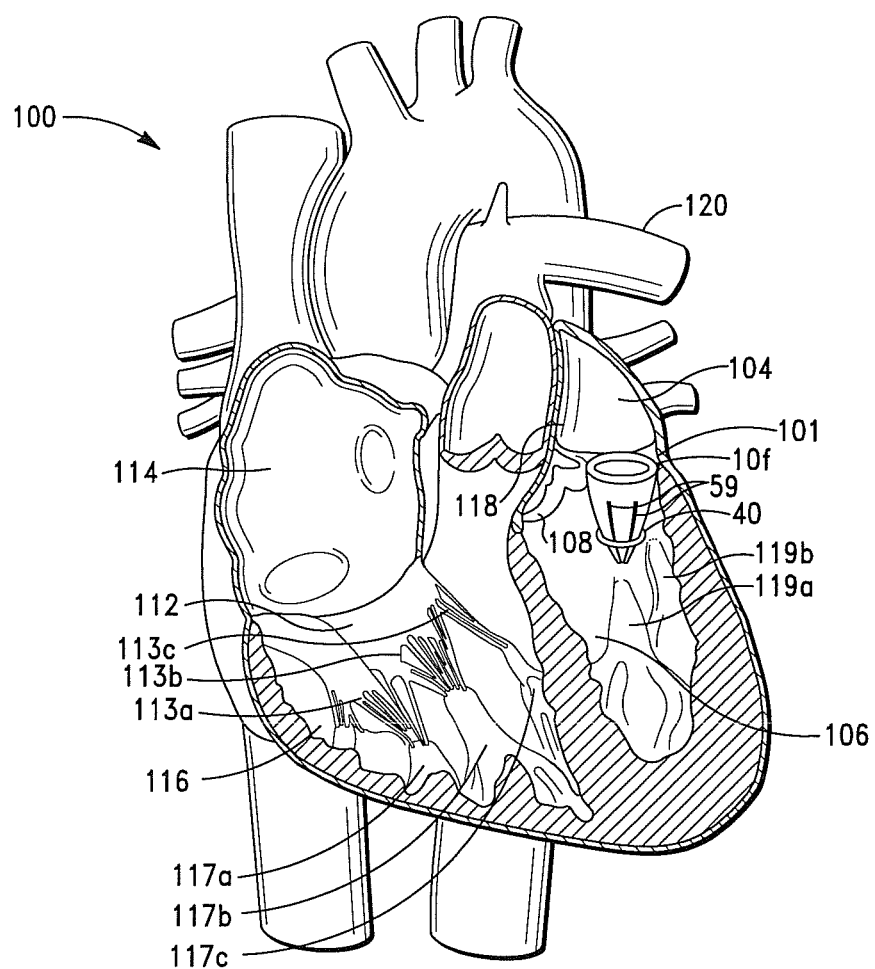
FIG. 10A is an illustration of the prosthetic "ribbon structure" valve shown in FIG. 7C secured to a mitral valve annulus region, in accordance with the invention.

According to the invention, when the prosthetic valves of the invention are engaged to a mitral valve annulus, such as illustrated in FIGS. 9A and 10A, and fluid, i.e., blood, comprising a positive fluid pressure is directed into the taper (or valve) regions of the prosthetic valves, as discussed in detail below, the prosthetic valves transition from a contracted configuration to an expanded configuration, wherein the flow modulating means thereof open and allow the blood to be transmitted through the valves and, thereby, into the left ventricle, and, when the blood exhibits a reduced pressure, the prosthetic valves transition from the expanded configuration to the contracted configuration, wherein the flow modulating means close and restrict blood from flowing through the valves and, hence, into the left ventricle.

As discussed in detail below, according to the invention, the transition of the prosthetic valves of the invention from the contracted configuration to the expanded configuration, and, thus opening of the flow modulating means, is induced by the positive fluid pressure of the blood directed into the taper regions of the prosthetic valves when the positive fluid pressure is sufficient to generate a first pressure differential between the internal valve pressure, i.e., pressure proximate the taper region of the prosthetic valve, and external pressure.

The transition of the prosthetic valves of the invention from the expanded configuration to the contracted configuration, and, thus closing of the flow modulating means, is induced when the reduced fluid pressure of the blood generates a second pressure differential between the internal valve pressure, i.e., pressure proximate the taper region of the prosthetic valve, and external pressure, the second pressure differential being lower than the first pressure differential.

Figures 3, 4A:
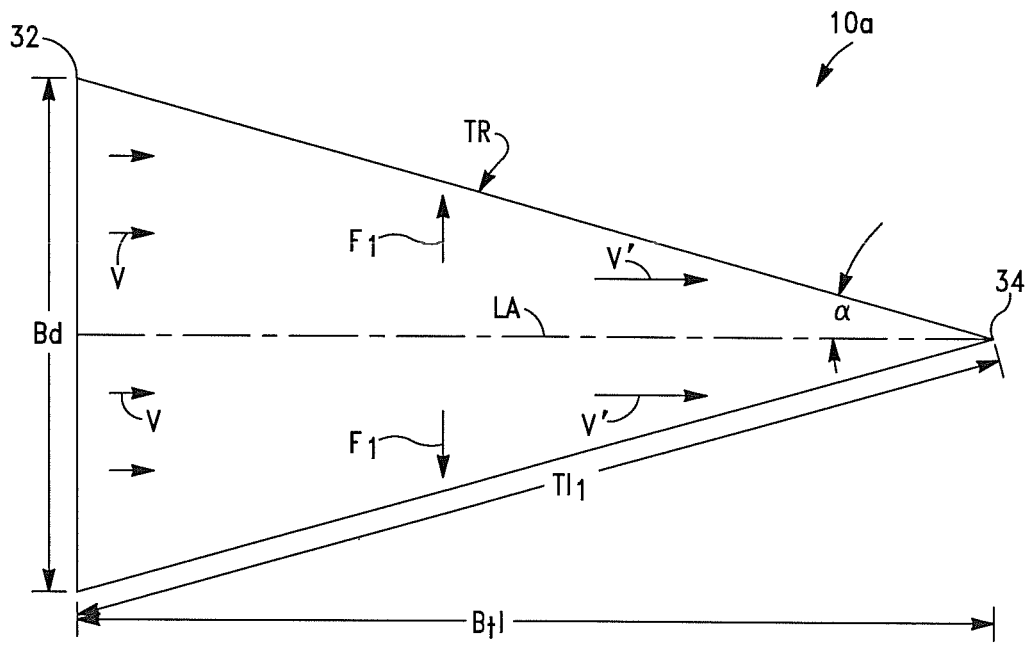
FIG. 3 is a list of nominal normal mitral valve measurements.
FIG. 4A is a schematic illustration of a prosthetic "sheet structure" valve, in accordance with the invention.
Figure 4B:
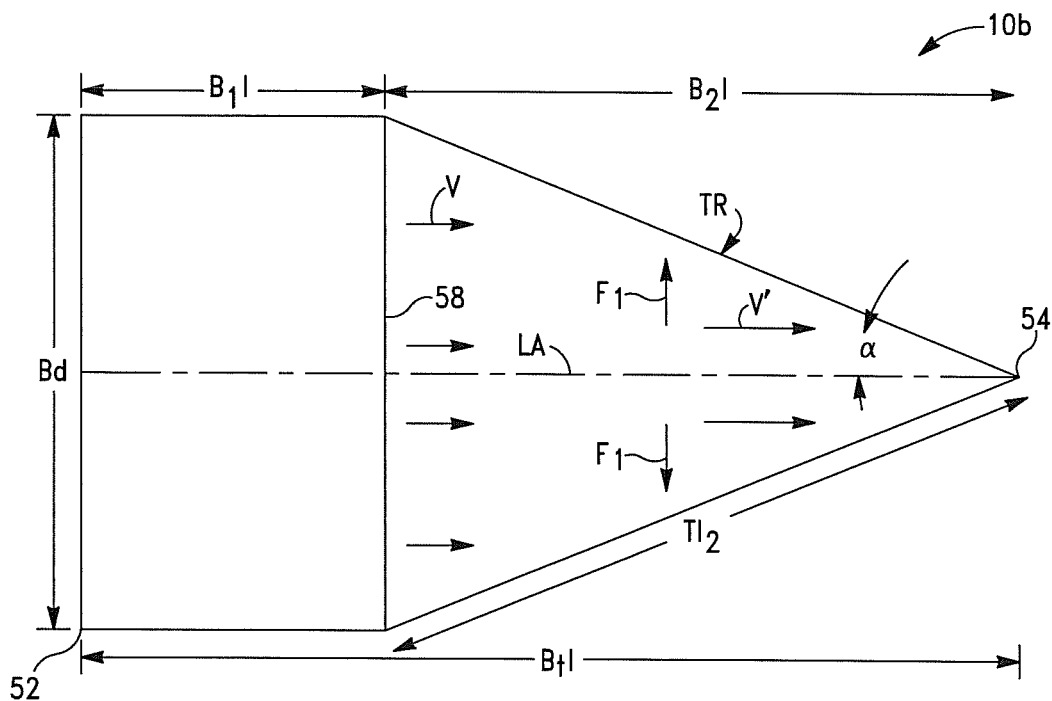
FIG. 4B is a schematic illustration of a prosthetic "ribbon structure" valve, in accordance with the invention.

As generally referenced above and shown in FIGS. 4A and 4B, the prosthetic valves of the invention comprise a conical shaped taper region (denoted "TR"). Thus, as discussed, below, based on the principle of continuity, blood flowing through the conical shaped regions of the prosthetic valves increases in velocity as the blood flows toward the distal ends of the valves, as denoted by Arrows V at the open proximal end and V' proximate the distal ends of the valves and, hence, flow modulating means thereof.

It is well established that the velocity of blood at the open proximal end of the prosthetic valves of the invention can be determined as follows:

$$v_1 = \frac{Q}{A_1} = \frac{Q}{\pi r_1^2} \qquad \text{Eq. 1}$$

where:
$v_1$=Velocity of blood at the open proximal end of the valve;
Q=Flow rate of the blood; and
$A_1$=Area of open proximal end of the valve.

It is also well established that, since blood is essentially incompressible, based on the principle of continuity, the same amount of blood must flow past any point within the conical shaped prosthetic valves of the invention in any given period of time and, hence, can be determined as follows:

$$v_2 = \frac{A_1}{A_2} v_1 = \frac{\pi r_1^2}{\pi r_2^2} v_1 = \frac{r_1^2}{r_2^2} v_1 \qquad \text{Eq. 2}$$

where:
$v_2$=Velocity of blood proximate the distal end of the valve;
$A_2$=Area of distal end of the valve.

By virtue of the enhanced blood velocity and, hence, flow achieved by virtue of the unique conical shape of the prosthetic valves of the invention, as discussed below, the prosthetic valves, when engaged to a mitral valve annulus, will (i) provide a blood flow rate into the left ventricle during atrial systole that is at least equivalent to, and, in some instances, greater than, the blood flow into the left ventricle during atrial systole with a native mitral valve, and (ii) can readily be adapted to open and direct blood into the left ventricle during atrial systole sooner than a native mitral valve subjected to an equivalent positive pulsatile fluid inflow pressure.

As will be readily apparent to one having ordinary skill in the art, the prosthetic valves of the invention provide numerous additional significant advantages compared to conventional prosthetic valves. Among the significant advantages are the following:

The provision of prosthetic valves; particularly, prosthetic mitral valves, which comprise an optimal sheet structure, including (i) an increased flow modulation means (i.e., leaflet) coaptation surface area compared to conventional prosthetic valve structures, which minimizes fluid; more specifically, blood flow, turbulence within the valve body, and (ii) an increased flow modulation means coaptation length compared to conventional prosthetic valve structures, which, when engaged to a mitral valve annulus, decreases the likelihood of regurgitation of blood into the left atrium during ventricular systole.

The provision of prosthetic valves; particularly, prosthetic mitral valves, which are fully functional without a support structure, e.g., stent frame, and, hence, do not comprise a support structure, which can, and in many instances will, disrupt blood flow through the outflow tract.

The provision of prosthetic valves; particularly, prosthetic mitral valves, which comprise a plurality of "independent" flow modulation means, whereby, if one flow modulation means is defective or fails, valve function is minimally disrupted, if at all.

The provision of prosthetic valves; particularly, prosthetic mitral valves, which, when engaged to a mitral valve annulus, are configured and adapted to provide a maximum blood flow rate across the mitral valve annulus region that is at least equivalent to, and, in some instances, greater than, the maximum blood flow rate across a mitral valve annulus region with a native mitral valve for a given period of time during a cardiac cycle.

The provision of prosthetic valves; particularly, prosthetic mitral valves, which, when engaged to a mitral valve annulus, are further configured and adapted to provide optimal blood flow characteristics of blood directed into the left ventricle and, thereby, optimal vortex dynamics inside the left ventricle.

Figure 1B:
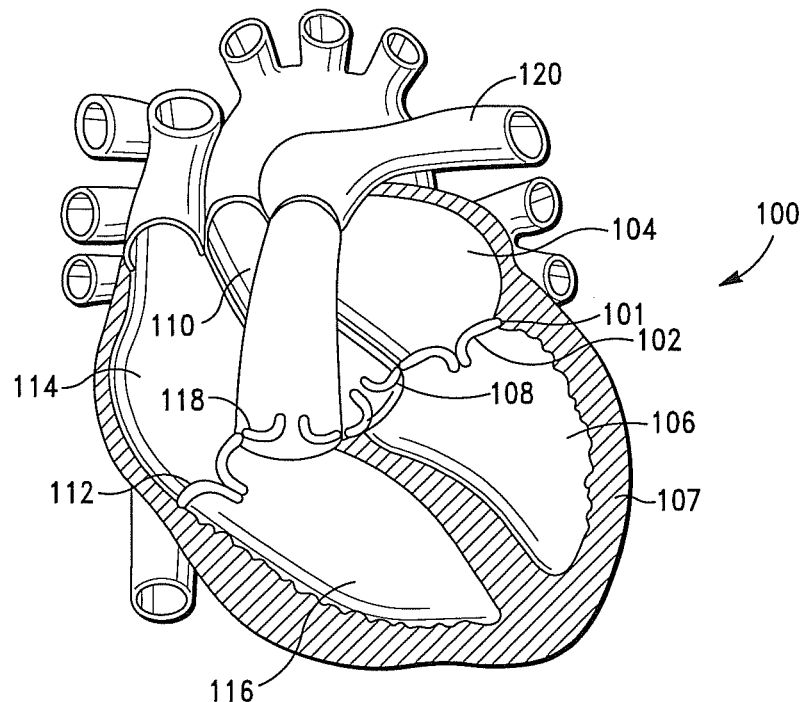
Figure 1C:
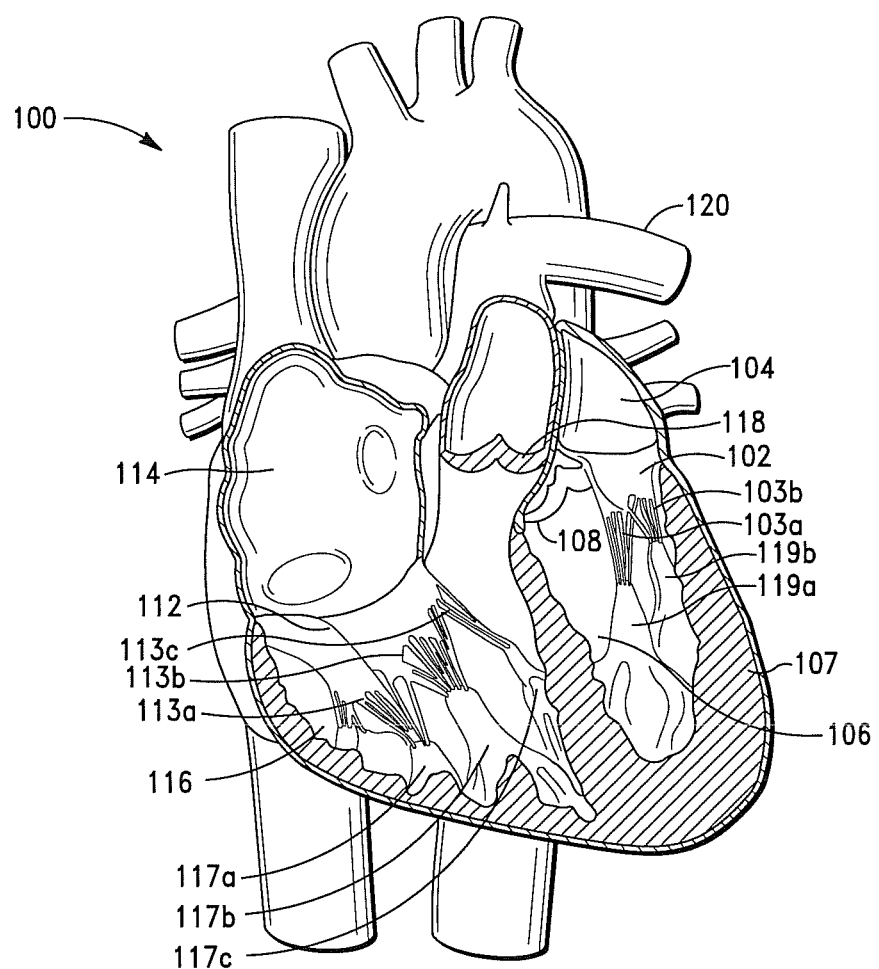
Figure 1G:
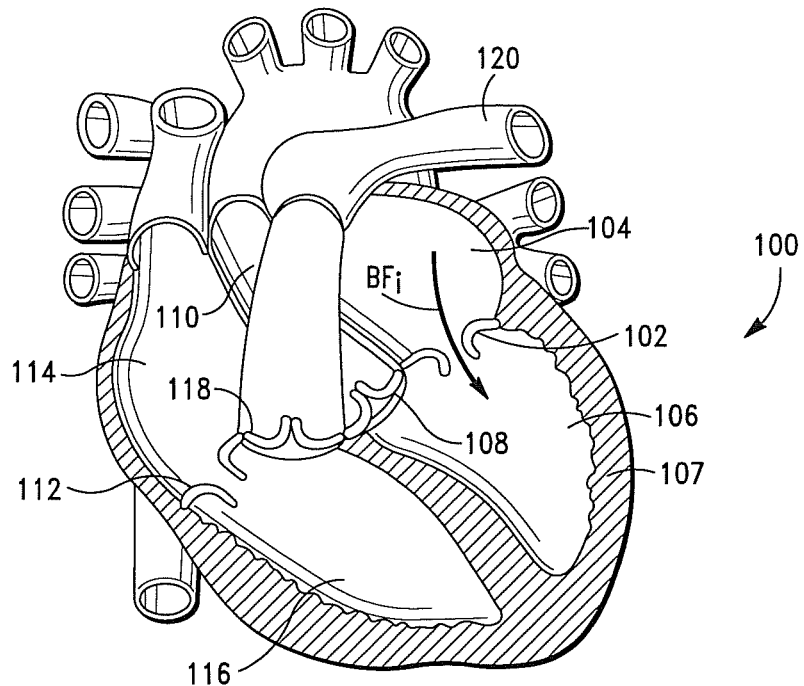
FIGS. 1G and 1H are further schematic illustrations of a human heart showing the blood flow proximate the mitral and aortic valves.
Figure 1H:
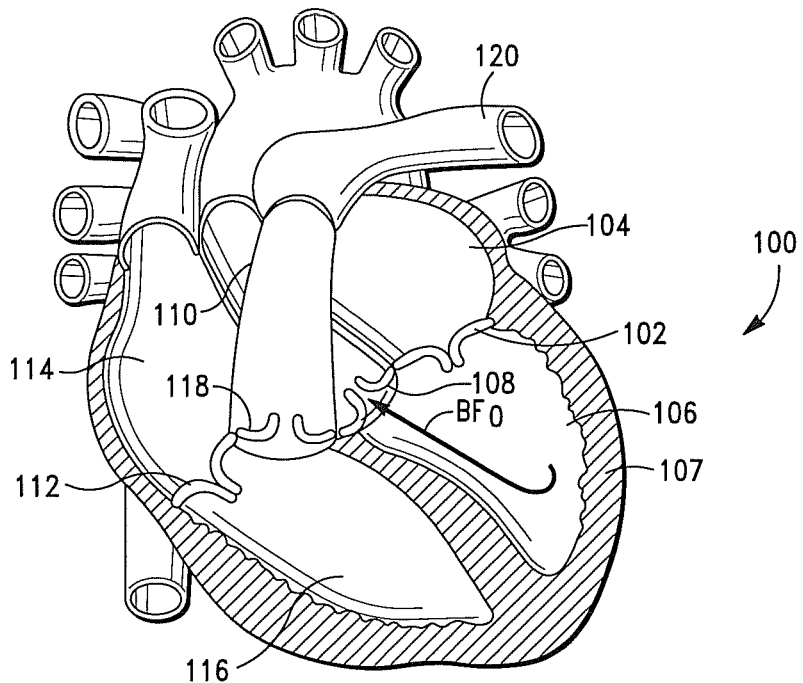

The provision of prosthetic valves; particularly, prosthetic mitral valves, which comprise a structure and configuration that substantially reduces disruption of blood flow out of the left ventricle and into and, hence, through the aortic valve, when engaged to a mitral valve annulus (see FIGS. 1G and 1H).

The provision of prosthetic valves; particularly, prosthetic mitral valves, which, when engaged to a mitral valve annulus, are further configured and adapted to provide a pressure half-time (PHT) that is at least equivalent to the PHT of a normal native mitral valve, i.e., the time interval in milliseconds between the maximum mitral gradient during ventricular diastole and the time point where the mitral gradient is half the maximum initial value.

The provision of prosthetic valves; particularly, prosthetic mitral valves, which can also be disposed in a mitral valve annulus and over native mitral valves without resection of the native leaflets or fixing the leaflets in an open configuration, which will allow the native leaflets to normally close during ventricular systole.

As indicated above, a significant advantage of the conical shaped prosthetic valves of the invention is that, by virtue of the increased coaptation length, when the prosthetic valves are operatively engaged to a mitral valve annulus, the prosthetic valves close more securely, which reduces the likelihood of regurgitation of blood into the left atrium during ventricular systole.

As discussed in detail below, according to the invention, the prosthetic valves of the invention can be further adapted to close sooner than a native mitral valve subjected to an equivalent negative left ventricle fluid pressure relative to the internal valve pressure, which further reduces the likelihood of regurgitation of blood into the left atrium during ventricular systole.

Figure 5A:
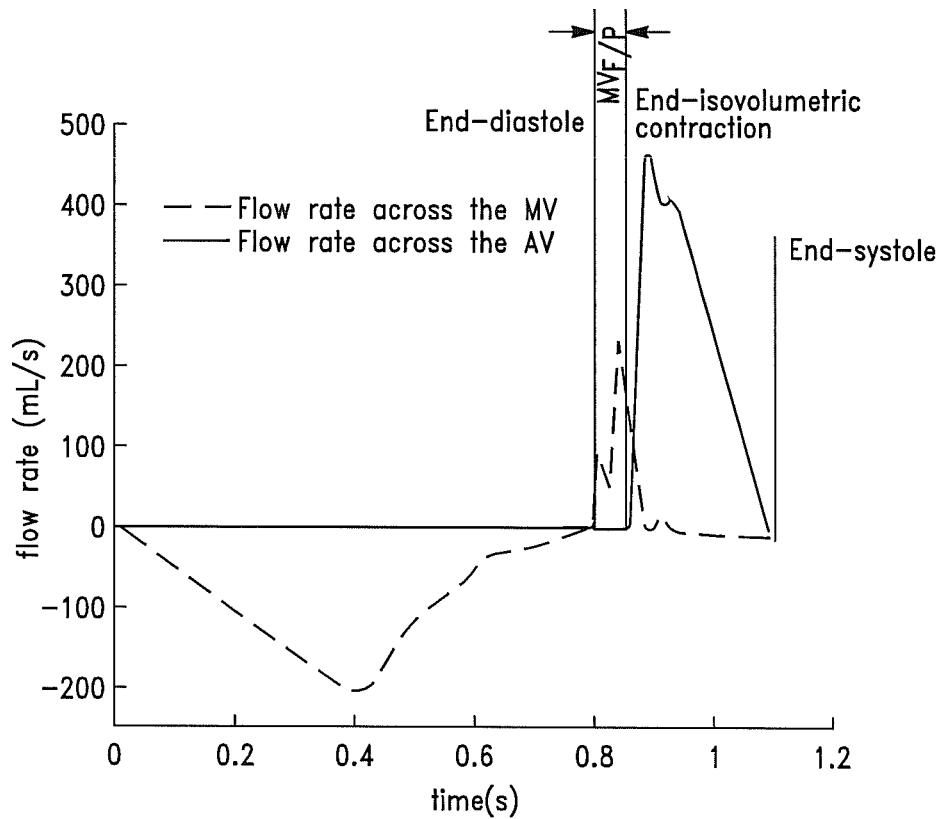
FIG. 5A is a graphical illustration of flow rate across the mitral and aortic valves.
Figure 5B:
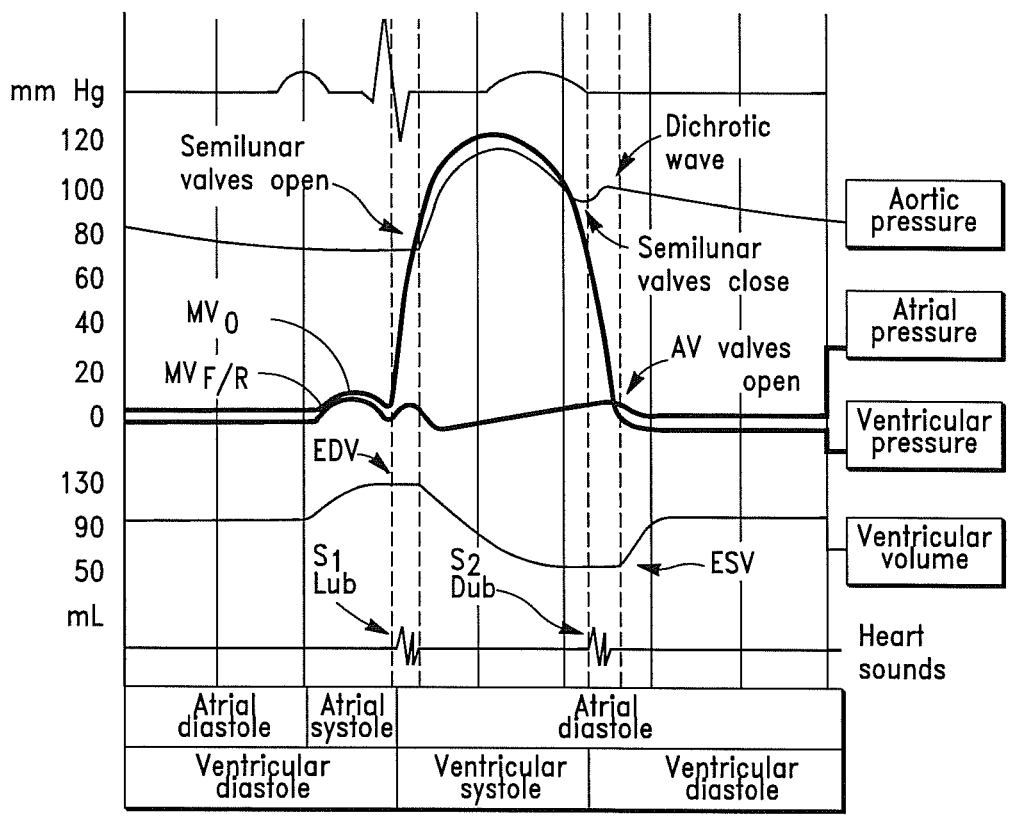
FIG. 5B is a graphical illustration of fluid pressure and heart valve function during a cardiac cycle for a normal adult male.
Figure 5C:
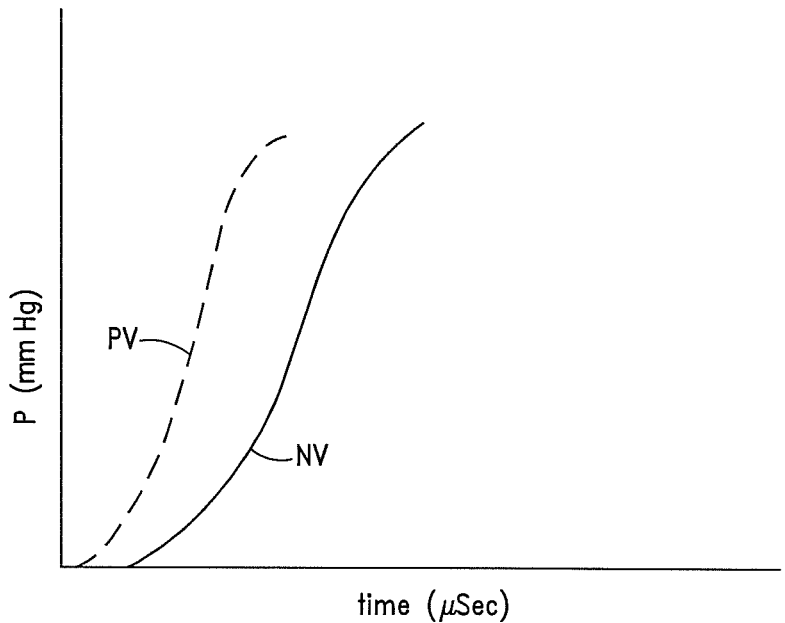
FIG. 5C is a graphical illustration of flow rate initiation out of a native mitral valve and one embodiment of a prosthetic valve as a function of time, in accordance with the invention.

As indicated above and illustrated in FIG. 5C, according to the invention, the prosthetic valves of the invention (denoted "PV") can further be adapted to open sooner during late ventricular diastole/atrial systole of a cardiac cycle and, thereby, direct blood into the left ventricle sooner than a native mitral valve (denoted "NV") subjected to an equivalent positive pulsatile fluid inflow pressure during the same cardiac cycle period.

Figure 2:
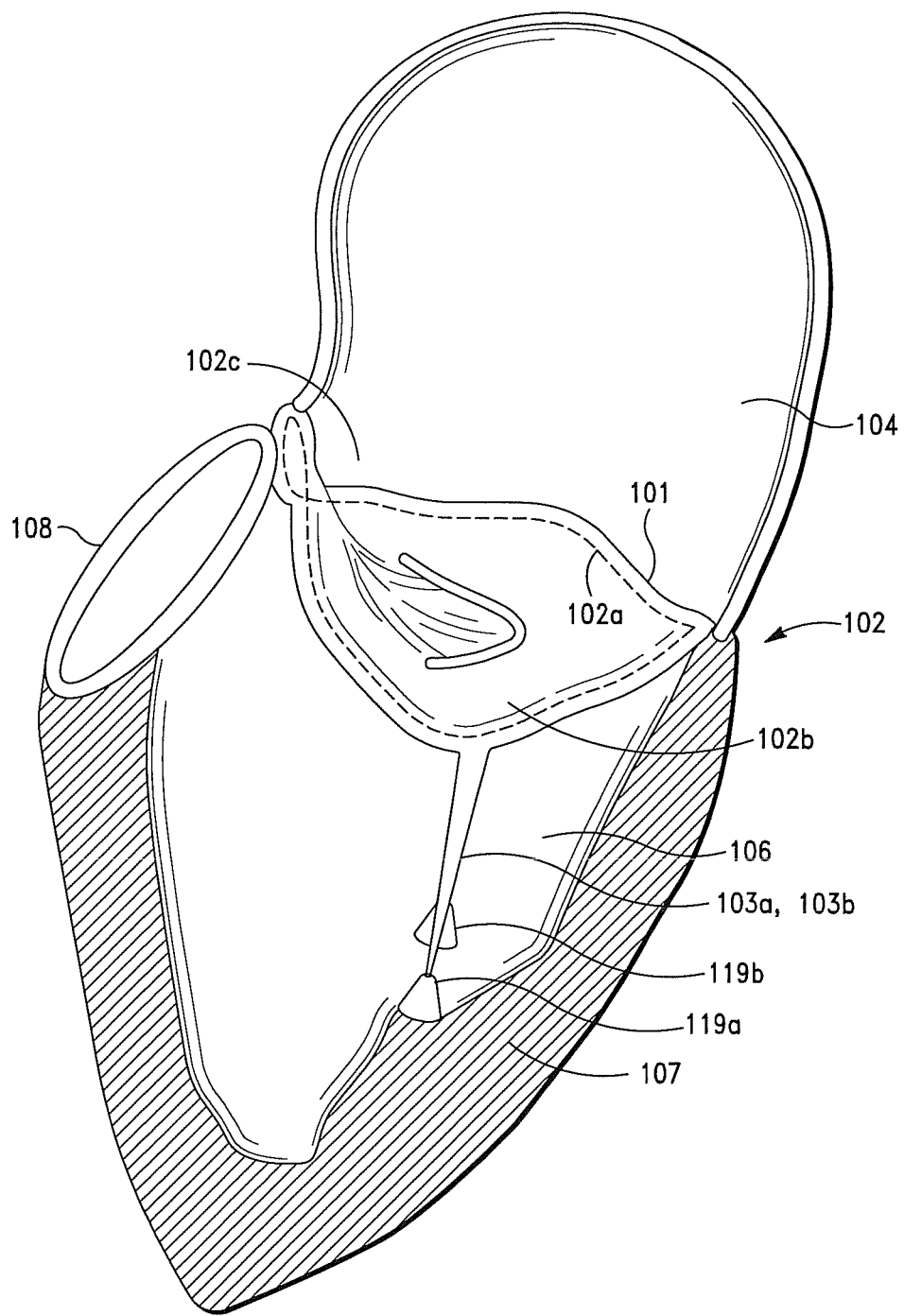
FIG. 2 is a further illustration of a mitral valve.

Referring now to FIG. 2, there is shown a schematic illustration of a native mitral valve 102 disposed in a mitral valve annulus 101. As indicated above and shown in FIGS. 1A and 1B, the mitral valve 102 is located between the left atrium 104 and the left ventricle 106 and controls blood flow between the left atrium 104 and the left ventricle 106 as a function of differential pressure therebetween.

As illustrated in FIG. 2, the mitral valve 102 comprises valve leaflets 102a, anterolateral commissure 102b, posteromedial commissure 102c and chordae 103a, 103b.

As further illustrated in FIG. 2, the cardiovascular structures associated with the mitral valve 102 include the papillary muscles 119a, 119b, to which the mitral valve 102 is engaged to, and the ventricular wall 107.

Referring now to FIG. 3, there is shown a table of measurements for a normal mitral valve. As discussed in detail below, the seminal measurements that are particularly applicable for the prosthetic mitral valves of the invention (referred to generally hereinafter as conical shaped "prosthetic valves" of the invention) are the mitral valve annulus dimensions and papillary muscles to annulus distances.

Referring now to FIGS. 4A and 4B, there are shown schematic illustrations of the conical shaped prosthetic valves of the invention. The preferred valve dimensions and configurations of the conical shaped prosthetic valves of the invention, which provide optimum function, will now be described in detail.

For purposes of describing the prosthetic valves of the invention and associated function, the parameters of the prosthetic valves provided herein are deemed suitable for conical shaped prosthetic tissue valves (i.e., prosthetic mitral valves) for a clinically healthy, i.e., normal, adult male patient having an age in the range of 21-34 years. However, according to the invention, the prosthetic valves of the invention can comprise various sizes and configurations to accommodate prosthetic mitral valves and other cardiovascular valves in patients of various ages and cardiac pathologies.

Referring first to FIG. 4A, there is shown a schematic illustration of the prosthetic "sheet structure" valves of the invention, denoted 10a.

According to the invention, for such a patient, the prosthetic valves 10a preferably comprise a total valve length (denoted "$B_t\ell$") in the range of approximately 20 mm to 45 mm.

In some embodiments of the invention, the prosthetic valves 10a comprise a valve length $B_t\ell$ in the range of approximately 20 mm to 35 mm.

The preferred total valve length ($B\ell$) of the prosthetic "sheet structure" valves 10a, i.e., 45 mm, allows for secure engagement of the proximal valve annulus engagement end 32 (see FIG. 6) of the valves 10a to the mitral valve annulus and positioning of the distal end 34 of the valves 10a proximate the papillary muscles 119a, 119b of an adult male heart for engagement thereto if desired.

According to the invention, the proximal valve annulus engagement end 32 of the prosthetic valves 10a preferably comprises a diameter, i.e., an operative valve diameter, (denoted "$B_d$") in the range of approximately 25.0 mm to 45.0 mm.

In a preferred embodiment, the prosthetic valves 10a comprise an operative valve diameter ($B_d$) in the range of approximately 38.0 mm to 40.0 mm.

The proximal valve annulus engagement end 32 of the prosthetic "sheet structure" valves of the invention thus preferably comprises a circumference in the range of approximately 119.4 mm to 125.7 mm.

In some embodiments of the invention, the ratio of the valve proximal valve annulus engagement end diameter ($B_d$) to valve length ($B_t\ell$) is thus preferably in the range of approximately 2:1 to 1:1.

The prosthetic valves 10a thus also preferably comprise an angle (denoted "α") relative to the longitudinal axis (denoted "LA") in the range of approximately 30-38°.

The taper length (denoted "$T\ell_1$") is thus preferably in the range of approximately 25.5 mm to 40.3 mm.

According to the invention, based on the preferred operative valve diameter ($B_d$) of approximately 38.0 mm to 40.0 mm and a taper length ($T\ell_1$) of approximately 25.5 mm to 40.3 mm, the prosthetic valves 10a will preferably comprise an in internal valve volume, i.e., operative valve volume, in the range of approximately 5.36 cm$^3$ to 14.6 cm$^3$, and an internal surface area ($A_s$) of 27.8 cm$^2$ to 37.9 cm$^2$.

Referring now to FIG. 4B, there is shown a schematic illustration of the prosthetic "ribbon structure" valves of the invention, denoted 10b.

In a preferred embodiment of the invention, the prosthetic "ribbon structure" valves 10b have a similar conical shaped valve region as the prosthetic "sheet structure" valves 10a. Thus, in a preferred embodiment, the prosthetic "ribbon structure" valves similarly comprise a conical valve region length (denoted "$B_2\ell$") in the range of approximately 10 mm to 45 mm. Preferably, the prosthetic valves 10b also similarly comprise a conical valve region length ($B_2\ell$) in the range of approximately 20 mm to 35 mm.

In a preferred embodiment, the proximal valve annulus engagement end 52 (see FIG. 7B) of the prosthetic "ribbon structure" valves 10b similarly comprise an operative valve diameter ($B_d$) in the range of approximately 25.0 mm to 45.0 mm. Preferably, the prosthetic valves 10b similarly comprise an operative valve diameter ($B_d$) in the range of approximately 38.0 mm to 40.0 mm.

The proximal valve annulus engagement end 52 of the prosthetic "ribbon structure" valves of the invention similarly preferably comprises a circumference in the range of approximately 119.4 mm to 125.7 mm.

The prosthetic valves 10b similarly preferably comprise a conical valve region angle ("α") relative to the longitudinal axis ("LA") in the range of approximately 30° to 38°, and taper length (denoted "$T\ell_2$") in the range of approximately 25.5 mm to 40.3 mm.

Preferably, the prosthetic valves 10b will similarly comprise an operative valve volume from the circumferential ribbon attachment region 58 to the distal end 54 of the valves 10b (i.e., taper region) in the range of approximately 5.36 cm$^3$ to 14.6 cm$^3$.

Again, based on the preferred operative valve diameter $B_d$ of approximately 38.0 mm to 40.0 mm and preferred taper length ($T\ell_2$) of approximately 25.5 mm to 40.3 mm, the taper region of the prosthetic valves 10b will similarly preferably comprise an internal valve volume, i.e., operative valve volume, in the range of approximately 5.36 cm$^3$ to 14.6 cm$^3$, and an internal surface area ($A_s$) of 27.8 cm$^2$ to 37.9 cm$^2$.

In a preferred embodiment of the invention, the prosthetic "ribbon structure" valves 10b further comprise (i) an annulus engagement region length (denoted "$B_1\ell$"), i.e., a length between the proximal valve annulus engagement end 52 and the circumferential ribbon connection region 58, in the range of 4 mm to 12 mm, more preferably, a length in the range of 8 mm to 10 mm, and, thus (ii) a total valve length ($B_t\ell$) in the range of approximately 15 mm to 55 mm, more preferably, a total valve length ($B_t\ell$) in the range of approximately 30 mm to 45 mm.

The total volume of the prosthetic valves 10b is thus preferably in the range of approximately 11.70 cm$^3$ to 27.20 cm$^3$.

Referring now to FIG. 5A, there is shown a graphical illustration of the nominal flow rate across the mitral valve throughout an entire cardiac cycle of a healthy adult male patient. As reflected in FIG. 5A, the typical nominal blood flow rate during a cardiac cycle of a healthy adult male patient ranges from approximately −200 mL/sec during ventricular diastole to approximately +225 mL/sec during ventricular systole.

As indicated above, in a preferred embodiment of the invention, for a given period of time; particularly, during ventricular diastole/atrial systole, the prosthetic valves of the invention are configured and adapted to provide a blood flow rate across a mitral valve annulus region and into the left ventricle that is at least equivalent to the blood flow rate across a mitral valve annulus region and into the left ventricle with a native mitral valve.

Referring now to FIG. 5B, there is shown a graphical illustration of fluid pressure and heart valve function during a cardiac cycle for a normal, healthy adult male. As illustrated in FIG. 5B, during late ventricular diastole/atrial systole, a native mitral valve and, hence, a prosthetic valve of the invention (when disposed in a mitral valve region), will be subjected to a peak blood flow from the left atrium (denoted "$MV_{F/P}$") with a peak pulsatile pressure, which, as discussed in further detail below, is generally <20 mm Hg (i.e., typically in the range of 10 mm Hg to 15 mm Hg) for a normal adult male.

As is well established and further illustrated in FIG. 5B, when a normal native mitral valve is subjected to the peak pulsatile pressure during late ventricular diastole/atrial systole, the native mitral valve opens (as denoted "MV" in FIG. 5B) and directs blood into the left ventricle.

According to the invention, during a normal cardiac cycle, such as illustrated in FIGS. 5A and 5B, when the prosthetic valves of the invention (which are graphically illustrated in FIGS. 4A and 4B) are engaged to a mitral valve region, such as illustrated in FIGS. 9A and 10A, as blood exhibiting the peak pulsatile pressure flows into the interior taper regions of the prosthetic valves during late ventricular diastole/atrial systole, whereby there is a positive pressure differential between the internal valvular pressure and the left ventricle pressure, outward internal forces resulting from the peak pulsatile pressure (denoted collectively "$F_1$" in FIGS. 4A and 4B) are exerted on the taper regions of the prosthetic valves (i.e., interior surfaces thereof), whereby, as discussed in detail below, the conical shaped prosthetic valves expand and the flow modulating means thereof open and direct the blood into the left ventricle.

As is also well established, the fluid pressure gradient across a mitral valve region during ventricular diastole (see FIG. 5B) for a healthy adult male is typically ≤4 mm Hg.

According to the invention, by virtue of the unique configuration of the prosthetic valves of the invention, the prosthetic valves, when operatively engaged to a mitral valve annulus (or any other valve annulus), will not increase the fluid pressure gradient across the valve annulus during a cardiac cycle.

As discussed in detail below, based on Applicant's proprietary computer model and associated algorithms, and employing the preferred dimensions of the prosthetic valves 10a and 10b (and, hence, prosthetic valves of the invention), referenced above, and an internal valvular pressure ("$P_{Int}$") in the range of approximately 10 mm Hg to 15 mm Hg, i.e., a pressure differential between the internal valvular pressure and external pressure in the range of approximately 10 mm Hg to 15 mm Hg ("$P_d$"), during late ventricular diastole/atrial systole of a cardiac cycle, when the prosthetic valves are operatively engaged to a mitral valve annulus, it is estimated that the outward force(s) exerted on the taper regions of the prosthetic valves of the invention will be in the range of approximately 3.71 N-5.05 N ($P_{Int}$=10 mm Hg and $A_S$=27.8 cm$^2$ to 37.9 cm$^2$) and 5.45 N-7.43 N ($P_{Int}$=15 mm Hg and $A_S$=27.8 cm$^2$ to 37.9 cm$^2$), which will expand the sheet structures, i.e., valve bodies of the prosthetic valves, and open the flow modulating means thereof and allow blood to be transmitted into the left ventricle.

As indicated above, in a preferred embodiment of the invention, when the prosthetic valves of the invention are operatively engaged to a mitral valve annulus, the prosthetic valves are adapted to provide (i) a blood flow rate across a mitral valve annulus region and into the left ventricle that is at least equivalent to the blood flow rate across a native mitral valve and into the left ventricle for a given period of time during a cardiac cycle, and (ii) a pressure half-time (PHT) is at least equivalent to the PHT of a normal native mitral valve.

Figure 6:
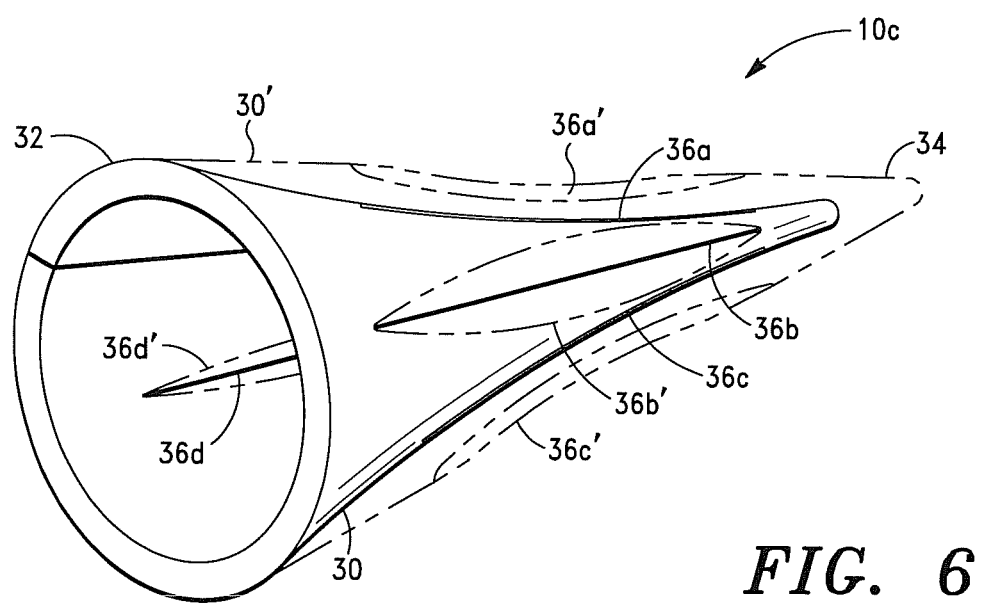
FIG. 6 is a perspective view of one embodiment of a prosthetic "sheet structure" valve, in accordance with the invention.
Figure 7A:
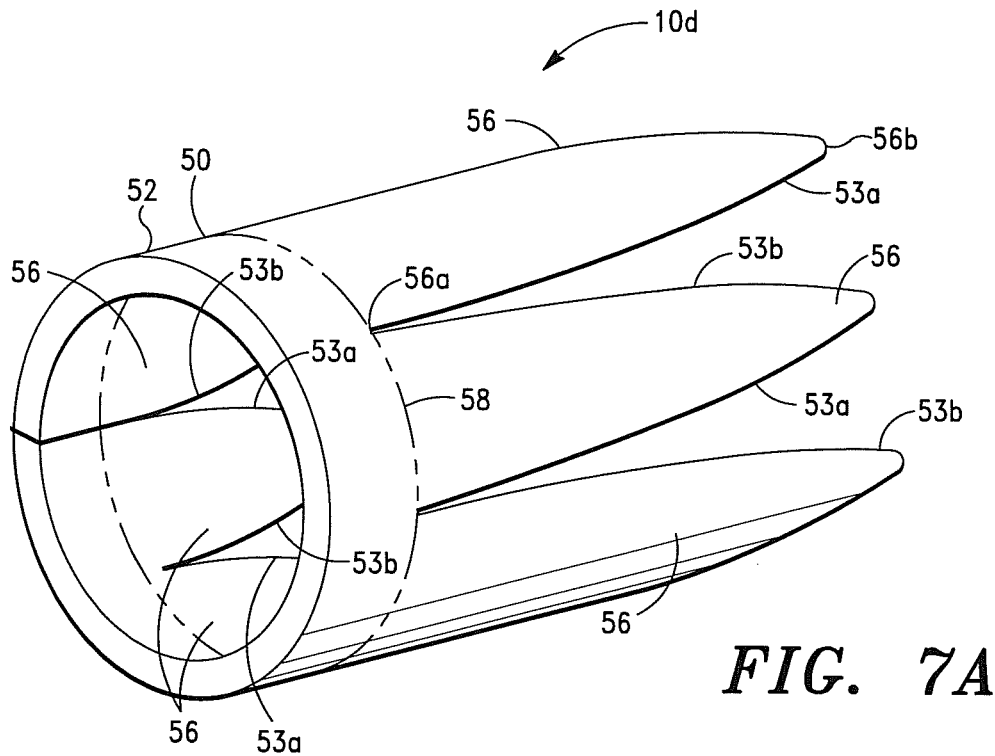
FIG. 7A is a perspective view of one embodiment of prosthetic "ribbon structure" valve, in accordance with the invention.
Figure 7B:
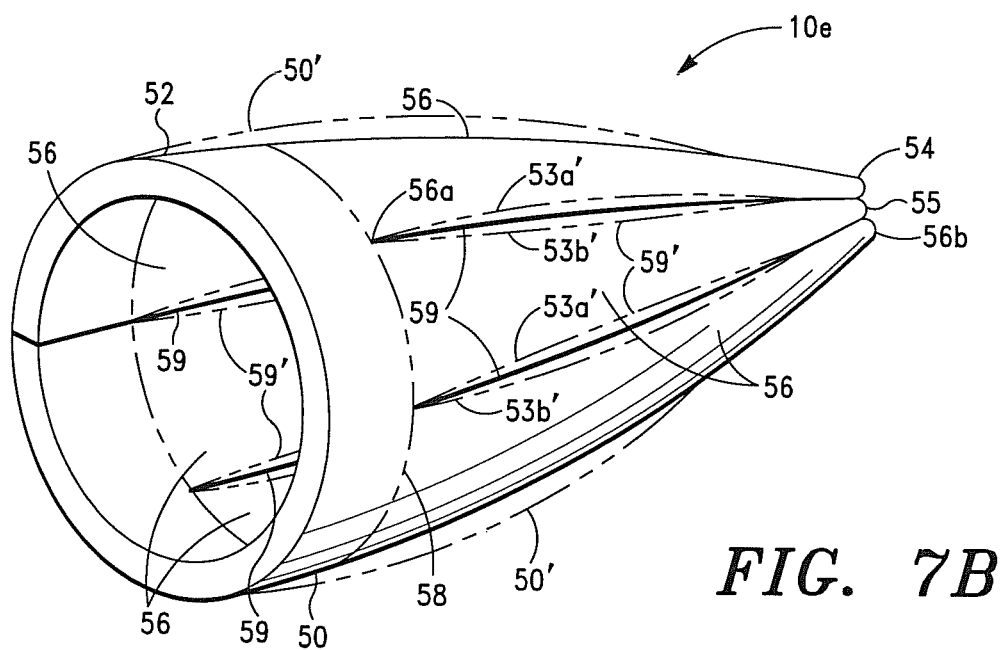
FIG. 7B is a perspective view of another embodiment of a prosthetic "ribbon structure" valve, in accordance with the invention.

In some embodiments of the invention, the total area of the flow modulating means of the prosthetic valves of the invention, when in a fully opened configuration (denoted "36a", "36b", "36c" in FIG. 6 and "59'" in FIG. 7B), is at least 2× greater than the inlet area defined by the open proximal annulus engagement ends of the prosthetic tissue valves of the invention (denoted "32" in FIG. 6 and "52" in FIG. 7B).

In some embodiments of the invention, when the prosthetic valves of the invention are operatively engaged to a mitral valve annulus, the prosthetic valves are thus adapted to provide a blood flow rate across a mitral valve annulus region and into the left ventricle during atrial systole that is greater than the blood flow rate across a mitral valve annulus region and into the left ventricle during atrial systole with a normal native mitral valve.

As indicated above, according to the invention, the prosthetic valves of the invention can be further adapted to achieve a maximum blood flow rate across a mitral valve annulus region and into the left ventricle during atrial systole sooner than a normal native mitral valve subjected to an equivalent blood inflow rate during atrial systole.

Indeed, in some embodiments of the invention, when a prosthetic valve of the invention, such as prosthetic valves 10c and 10e shown in FIGS. 6 and 7B, respectively, is engaged to a mitral valve region, such as shown in FIGS. 9A and 10A, and there is a positive pressure differential between the internal valvular pressure and the left ventricle pressure >4 mm Hg, the prosthetic valve directs a blood flow rate of at least 200 mL/sec into the left ventricle during atrial systole in <40 milliseconds.

As indicated above, according to the invention, the prosthetic valves of the invention can be further adapted to open sooner (i.e., the flow modulating regions thereof open sooner) and, thereby, direct blood into the left ventricle when subjected to a positive pulsatile fluid pressure during late ventricular diastole/atrial systole (i.e., when there is a positive pressure differential between the internal valvular pressure and the left ventricle pressure) than a normal, native mitral valve that is subjected to an equivalent positive pulsatile fluid pressure during late ventricular diastole/atrial systole.

In a preferred embodiment of the invention, when the prosthetic valves of the invention are engaged to a mitral valve region, the prosthetic valves are additional adapted to close more securely during ventricular systole than a normal, native mitral valve during ventricular systole (where the native mitral valve is subjected to an equivalent negative left ventricle fluid pressure relative to the internal valve pressure), whereby regurgitation of blood into the left atrium is substantially reduced or eliminated.

It has also been established that the direction (angle) of the inflow of blood from the mitral valve affects the vortex dynamics inside the heart and even reverse its direction of motion. See G. Pedrizzetti, et al., "*On the Left Ventricular Vortex Reversal After Mitral Valve Replacement*," Annals of Biomedical Engineering, vol. 38, no. 3, pp. 769-773 (2010).

Mitral valves not only affect the direction of the mitral jet into the left ventricle but also can create vortex shedding that affects the vortex dynamics inside the left ventricle. See R. Faludi, et al., "*Left Ventricular Flow Patterns in Healthy Subjects and Patients with Prosthetic Mitral Valves: An In Vivo Study Using Echocardiographic Particle Image Velocimetry*," Journal of Thoracic and Cardiovascular Surgery, vol. 139, no. 6, pp. 1501-1510 (2010).

According to the invention, the prosthetic valves of the invention are further adapted to provide optimal blood flow characteristics of blood flow directed into the left ventricle and, thereby, optimal vortex dynamics inside the left ventricle during late ventricular diastole/atrial systole.

Indeed, in a preferred embodiment, the prosthetic valves of the invention substantially reduce blood flow turbulence in the left ventricle during late ventricular diastole/atrial systole, which is often presented with conventional prosthetic valves; particularly, prosthetic valves that comprise sewing rings, as well as defective native mitral valves.

As indicated above, the prosthetic valves of the invention can comprise and, hence, be formed with various biocompatible materials and compositions. In a preferred embodiment, the biomaterials and compositions are employed to form sheet structures, which are then used to form the conical shaped prosthetic valves of the invention.

In some embodiments of the invention, the prosthetic valves are formed from and, hence, comprise an ECM composition comprising acellular ECM from a mammalian tissue source, such as the conical shaped prosthetic tissue valves disclosed in Applicant's U.S. Pat. Nos. 10,052,409, 10,188,509, 10,188,510 and 10,188,513, and Co-pending U.S. application Ser. Nos. 16/129,968, 16/440,504 and 16/553,499, which are incorporated by reference herein in their entirety.

In some embodiments of the invention, the prosthetic valves of the invention are formed from and, hence, comprise a polymeric composition comprising at least one polymer; preferably, a biocompatible polymer.

According to the invention, suitable biocompatible polymers include, without limitation, polyurethane urea, including porous polyurethane urea (Artelon®), polypropylene, poly(s-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™), and polyethylene terephthalate (Dacron™).

In some embodiments of the invention, the biocompatible polymer comprises a natural polymer.

According to the invention, suitable natural polymers include, without limitation, polysaccharides (e.g., starch and cellulose), proteins (e.g., gelatin, casein, silk, wool, etc.), and polyesters (e.g., polyhydroxyalkanoates).

In some embodiments of the invention, the polymeric composition (and, hence, prosthetic tissue valves formed therefrom) further comprises at least one additional biologically active agent or composition, i.e., an agent that induces or modulates a physiological or biological process, or cellular activity, e.g., induces proliferation, and/or growth and/or regeneration of tissue.

According to the invention, suitable biologically active agents include any of the aforementioned biologically active agents, including, without limitation, the aforementioned growth factors, cells and proteins.

Thus, in some embodiments of the invention, the biologically active agent comprises a growth factor, including, without limitation, transforming growth factor beta (TGF-β), fibroblast growth factor-2 (FGF-2) (also referred to as basic fibroblast growth factor), and vascular endothelial growth factor (VEGF).

In some embodiments, the biologically active agent comprises an exosome, such as the exosomes disclosed in Applicant's priority application Ser. No. 16/129,968 and the exosomes disclosed in Applicant's U.S. Pat. No. 10,143,778 and co-pending U.S. application Ser. No. 16/990,576.

In some embodiments of the invention, the polymeric composition (and, hence, prosthetic tissue valves formed therefrom) further comprises at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned pharmacological agents and agents set forth in Applicant's U.S. application Ser. No. 15/206,833, now U.S. Pat. No. 10,188,510.

In a preferred embodiment of the invention, the prosthetic valves of the invention are formed with and, hence, comprise a collagenous tissue derived from a mammalian tissue source, i.e., a collagenous mammalian tissue.

As indicated above, the collagenous mammalian tissue can be similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

In a preferred embodiment of the invention, the collagenous mammalian tissue comprises heart or cardiac tissue.

In some embodiments of the invention, the cardiac tissue comprises pericardium tissue.

In some embodiments of the invention, the mammalian tissue source comprises a bovine tissue source, e.g., bovine pericardium tissue.

In some embodiments of the invention, the mammalian tissue source comprises a porcine tissue source, e.g., porcine pericardium tissue.

In some embodiments, the mammalian tissue source comprises an adolescent mammalian tissue source, i.e., tissue derived from a mammal less than 3 years of age.

In some embodiments of the invention, the collagenous mammalian tissue is derived from a mammalian tissue source that is devoid of xenogeneic antigens.

In some embodiments, the collagenous mammalian tissue thus comprises collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetyl-neuraminic acid hydroxylase, swine leukocyte antigen class I and porcine endogenous retrovirus polymerase (referred to hereinafter as "immune privileged collagenous mammalian tissue").

In some embodiments, the immune privileged collagenous mammalian tissue is derived from a genetically modified organism, such as, by way of example, a genetically modified pig and/or bovine.

In some embodiments, the immune privileged collagenous mammalian tissue is thus derived from a genetically modified pig.

In some embodiments, the genetically modified pig comprises a pig originating from at least one porcine germline cell, e.g., embryo, that has been genetically altered or reconstructed to knockout or delete at least one porcine gene that encodes for a xenogeneic antigen product.

According to the invention, the genetic alteration or reconstruction of a germline cell; more specifically, a porcine embryo can be done according to any conventional gene editing method, such as conventional gene editing methods that employ clustered regularly interspaced short palindromic repeats (CRISPR)-Cas9, Transcription Activator-like Effector Nucleases (TALEN) or RNA interference.

In some embodiments, the knockout or deletion of a gene in a porcine embryo and, hence, pig developed therefrom is done according to the CRISPR-Cas9 gene editing method described in Niu, et al., *Inactivation of Porcine Endogenous Retrovirus in Pigs Using CRISPR-Cas9*, Science, vol. 357, no. 6357, pp. 1303-1307 (2017), which is incorporated by reference herein in its entirety.

According to the invention, the noted gene editing methods can be adapted and configured to knockout or delete any genes in a porcine embryo that encode for xenogeneic antigens including, without limitation, GGTA1 (galactose-alpha-1,3-galactose), β4GalNT2 (beta-1,4 N-acetylgalactosaminyltransferase 2), CD46 (membrane cofactor protein), ASGR1 (hepatic lectin H1), CMAH (cytidine monophospho-N-acetylneuraminic acid hydroxylase), SLA class I (swine leukocyte antigen class I) and PERV pol (porcine endogenous retrovirus polymerase) gene.

In a preferred embodiment, the collagenous mammalian tissue is derived from mammalian tissue of a pig developed from an embryo that has been genetically altered by knocking out or deleting the genes GGTA1, β4GalNT2 and CMAH, which encode for the xenogeneic antigen products galactose-alpha-1,3-galactose, beta-1,4 N-acetylgalactosaminyltransferase 2 and cytidine monophospho-N-acetylneuraminic acid hydroxylase, respectively.

According to the invention, the likelihood of inducing an adverse immune response, including adverse immune responses associated with xenogeneic tissue graft rejection, in vivo with the above referenced immune privileged collagenous mammalian tissue is minimal.

In some embodiments of the invention, the collagenous mammalian tissue (and, hence, prosthetic tissue valve formed therefrom) further comprises at least one additional biologically active agent or composition, i.e., an agent that induces or modulates a physiological or biological process, or cellular activity.

According to the invention, suitable biologically active agents similarly include any of the aforementioned biologically active agents, including, without limitation, the aforementioned growth factors, cells and proteins.

In some embodiments of the invention, the collagenous mammalian tissue (and, hence, prosthetic tissue valve formed therefrom) further comprises at least one of the aforementioned pharmacological agents and agents set forth in Applicant's U.S. application Ser. No. 15/206,833, now U.S. Pat. No. 10,188,510.

According to the invention, the collagenous mammalian tissue can comprise any suitable thickness. In some embodiments, the collagenous mammalian tissue comprises a thickness in the range of approximately 0.1 mm to 5.0 mm.

In a preferred embodiment of the invention, the collagenous mammalian tissue comprises a thickness in the range of approximately 0.2 mm to 1.0 mm.

In a preferred embodiment, the collagenous mammalian tissue comprises crosslinked collagenous mammalian tissue.

According to the invention, the collagenous mammalian tissue can crosslinked by various conventional means.

In a preferred embodiment, the collagenous mammalian tissue is crosslinked by subjecting the mammalian tissue to a suitable crosslinking agent (i.e., incubating the mammalian tissue in a suitable crosslinking agent or solution thereof), whereby the tissue exhibits bonded or crosslinked collagen fibrils and, thereby, increased tensile strength compared to natural, unprocessed mammalian tissue.

According to the invention, the collagenous mammalian tissue can be crosslinked with any suitable crosslinking agent, including, without limitation, glutaraldehyde, genipin, 1-ethyl-3-(3-dimethylaminopropyl) carbodiimide hydrochloride (EDC), nordihydroguaiaretic acid (NDGA), tannin acid, six methylene diisocyanate and glycerin.

In one embodiment of the invention, the collagenous mammalian tissue is processed, i.e., crosslinked, with glutaraldehyde (referred to herein after as "GA processed mammalian tissue"). Although GA processed mammalian tissue will typically exhibit enhanced mechanical properties; particularly, enhanced tensile strength, conventional GA processed mammalian tissue and, hence, prostheses formed therewith, will often present calcification and cytotoxicity issues in vivo.

It has, however, been found that the calcification and cytotoxicity issues associated with GA processed mammalian tissue in vivo can be addressed, i.e., substantially reduced or eliminated, by treating GA processed mammalian tissue with one or more stabilizing solutions during the glutaraldehyde processing.

In some embodiments, after treating the mammalian tissue with a 0.5% glutaraldehyde solution, the GA processed mammalian tissue is treated with an L-glutamic acid stabilizing solution. In a preferred embodiment, the L-glutamic acid stabilizing solution comprises $2.0$-$3.0*10^{-2}$ mol/L L-glutamic acid and $4.0$-$6.0*10^{-3}$ mol/L sodium borate.

Thus, in one preferred embodiment, the collagenous mammalian tissue is processed via the following steps:
 (i) incubating the collagenous mammalian tissue at 37° C. in an isotonic tris-buffer, such as a solution comprising 10-50 µg/mL of RNAse and 0.2-0.5 µg/mL DNAse with 5 mM ethylenediaminetetraacetic acid (EDTA);
 (ii) rinsing the collagenous mammalian tissue with phosphate buffered saline, such as Dulbecco's Phosphate Buffered Saline (DPBS);
 (iii) incubating the collagenous mammalian tissue in a 0.05-0.5% glutaraldehyde (GA) solution with 5 mM EDTA in DPBS;
 (iv) rinsing the collagenous mammalian tissue again with DPBS;
 (v) incubating the collagenous mammalian tissue in a L-glutamic acid stabilizing solution comprising $2.0$-$3.0*10^{-2}$ mol/L L-glutamic acid and $4.0$-$6.0*10^{-3}$ mol/L sodium borate with 5 mM EDTA in DPBS; and (vi) rinsing the collagenous mammalian tissue a final time with DPBS.

It has additionally been found that the calcification and cytotoxicity issues associated with GA processed mammalian tissue in vivo can similarly be addressed by treating the GA processed mammalian tissue with a carboxyl activating agent, such as 1-ethyl-3-(3-dimethylaminopropyl)-carbodiimide hydrochloride (EDC), dihexylcarbodiimide (DCC) and 1-ethyl-3-(4-azonia-4,4-dimethylpentyl) carbodiimide iodide (EAC), which will cause the carboxyl (COOH) groups present on the collagen molecules to be converted to activated carboxyl moieties (e.g., o-acylisourea), and immediately after treating the GA processed mammalian tissue with a carboxyl activating agent, treating the tissue with a non-carboxyl agent, such as an amine, e.g., propyl amine, ethylene diamine, etc., which reacts with the activated carboxyl moieties (e.g., o-acylisourea) formed via the carboxyl activating agent treatment to form non-carboxyl side groups on the collagen molecules in place of the previously existing carboxyl (COOH) groups.

In a preferred embodiment of the invention, the carboxyl agent comprises 1-ethyl-3-(3-dimethylaminopropyl)-carbodiimide hydrochloride (EDC) and the non-carboxyl agent comprises propyl amine.

Thus, in another preferred embodiment, the collagenous mammalian tissue is processed via the following steps:
(i) incubating the collagenous mammalian tissue at 37° C. in an isotonic tris-buffer, such as a solution comprising 10-50 µg/mL of RNAse and 0.2-0.5 µg/mL DNAse with 5 mM EDTA;
(ii) rinsing the collagenous mammalian tissue with DPBS;
(iii) incubating the collagenous mammalian tissue in a 0.05-0.5% glutaraldehyde (GA) solution with 5 mM EDTA in DPBS;
(iv) rinsing the collagenous mammalian tissue again with DPBS;
(v) incubating the collagenous mammalian tissue in a carboxyl activating agent comprising EDC;
(vi) rinsing the collagenous mammalian tissue again with DPBS;
(vii) incubating the collagenous mammalian tissue in a non-carboxyl agent comprising propyl amine; and
(viii) rinsing the collagenous mammalian tissue a final time with DPBS.

According to the invention, collagenous mammalian tissue subjected to one of the aforementioned GA processing methods of the invention, i.e., GA processed mammalian tissue, will exhibit minimal cytotoxicity and calcification in vivo.

The GA processed mammalian tissue will also exhibit the following physical characteristics:
(i) a tensile strength in the range of 9.0-12.0 MPa; and
(ii) an elastic phase slope, i.e., modulus (E), in the range of approximately 0.3 MPa to 0.9 MPa, depending on the incubation time of the collagenous mammalian tissue in the GA solution.

In a preferred embodiment, the collagenous mammalian tissue is incubated in the GA solution for a period of time in the range of for 24-48 hours, wherein the GA processed mammalian tissue exhibits an elastic phase slope in the range of approximately 0.3 MPa to 0.5 MPa.

In another preferred embodiment of the invention, the mammalian tissue is processed, i.e., crosslinked, with a procyanidin solution (referred to herein after as "PA processed mammalian tissue").

It has been found that procyanidin not only has the ability to stabilize extracellular matrix-derived scaffolds that primarily rely on hydrogen bonding, but also adds antioxidant and pharmacological activity to such scaffolds due to its ability to absorb free radicals.

Thus, in another preferred embodiment, the collagenous mammalian tissue is processed via the following steps:
(i) incubating the collagenous mammalian tissue at 37° C. in an isotonic tris-buffer, such as a solution comprising 10-50 µg/mL of RNAse and 0.2-0.5 µg/mL DNAse with 5 mM EDTA;
(ii) rinsing the collagenous mammalian tissue with DPBS;
(iii) incubating the collagenous mammalian tissue in a 0.1-0.5 wt % procyanidin solution with 5 mM EDTA in DPBS for a period of time in the range of 1-48 hrs; and
(iv) rinsing the collagenous mammalian tissue a final time with DPBS.

In a preferred embodiment of the invention, the PA processed mammalian tissue will similarly exhibit minimal cytotoxicity and calcification in vivo. The PA processed mammalian tissue will also exhibit a tensile strength of approximately 19.0 MPa to 22.0 MPa, which is approximately 70% greater than natural, untreated mammalian tissue, and an elastic phase slope comparable to the GA processed mammalian tissue of the invention.

According to the invention, the collagenous mammalian tissue can also be sterilized according to any conventional method, such as the methods disclosed in Applicant's U.S. application Ser. No. 13/480,205, and U.S. Pat. Nos. 8,845, 719, 9,226,821 and 8,877,224, which are incorporated by reference herein in their entirety.

In some embodiments of the invention, the collagenous mammalian tissue is processed or sterilized (post-GA or PA processing, or solely) via Applicant's proprietary Novasterilis™ process disclosed in U.S. Pat. Nos. 7,108,832, 8,034,288 and 8,974,730, which are incorporated by reference herein.

In some embodiments of the invention, the aforementioned supplemental biologically active agents and pharmacological agents are introduced into the collagenous mammalian tissue via Applicant's proprietary Novasterilis™ process.

Thus, as indicated above, in some embodiments of the invention, the collagenous mammalian tissue comprises at least one of the aforementioned biologically active agents and/or pharmacological agents and compositions formed therefrom.

In some embodiments of the invention, it is thus contemplated that, following placement of a prosthetic valve of the invention that comprises a collagenous mammalian tissue (referred to hereinafter as a "prosthetic collagenous tissue valve") or a polymeric composition (referred to hereinafter as a "prosthetic polymeric valve") on or in a cardiovascular structure (or structures) in a subject and, hence, cardiovascular tissue associated therewith, the prosthetic valve will induce "modulated healing" of the cardiovascular structure(s) and cardiovascular tissue associated therewith.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect.

Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, a prosthetic collagenous tissue valve or prosthetic polymer valve of the invention is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of a prosthetic conical shaped collagenous tissue valve or prosthetic conical shaped polymer valve of the invention to restrict the expression of inflammatory components.

By way of example, according to the invention, when a prosthetic collagenous tissue valve or prosthetic polymer valve (and/or annular ring and/or structural ring) of the invention comprises a statin and the prosthetic collagenous tissue valve or prosthetic polymer valve is positioned proximate damaged tissue, e.g., attached to a valve annulus, the valve restricts expression of monocyte chemoattractant protein-1 (MCP-1) and chemokine (C-C) motif ligand 2 (CCR2).

By way of further example, according to the invention, when a prosthetic collagenous tissue valve of the invention comprises an immune privileged collagenous mammalian tissue, as defined herein, and the prosthetic collagenous tissue valve is positioned proximate damaged tissue, e.g., attached to a valve annulus, the valve will not induce an adverse immune response; particularly, an immune response associated with tissue prosthesis rejection in vivo.

In some embodiments of the invention, "modulated healing" means and includes the ability of a prosthetic collagenous tissue valve or prosthetic polymer valve of the invention to alter a substantial inflammatory phase (e.g., platelet or fibrin deposition) at the beginning of the tissue healing process. As used herein, the phrase "alter a substantial inflammatory phase" refers to the ability of a prosthetic valve of the invention to substantially reduce the inflammatory response at a damaged tissue site, e.g., valve annulus, when in contact with tissue at the site.

The term "modulated healing" also refers to the ability of a prosthetic collagenous tissue valve or prosthetic polymer valve of the invention to induce cell migration, and cell and host tissue proliferation when disposed proximate damaged tissue, e.g., valve annulus.

Referring now to FIG. 6, there is shown one embodiment of a prosthetic "sheet structure" valve of the invention, denoted 10c.

Asset forth in Applicant's U.S. Pat. Nos. 10,188,509 and 10,188,510, which are incorporated by reference herein, and illustrated in FIG. 6, the prosthetic valve 10c preferably comprises proximal and distal ends 32, 34, and a plurality of flow modulation means, i.e., open regions or interstices, 36a-36d that are preferably disposed linearly over a portion of the length of the valve 10c.

As also set forth in Applicant's U.S. Pat. Nos. 10,188,509 and 10,188,510, the interstices 36a-36d can comprise a length that is in the range of approximately 10% to 98% of the overall length of the valve 10c. In a preferred embodiment, the interstices 36a-36d comprise a length that is in the range of approximately 50% to 98% of the length of the valve 10c (denoted "$B_t\ell$" in FIG. 4A).

Preferably, the distal ends of the interstices 36a-36d are disposed proximate the distal end 34 of the conical shaped member 30 and, hence, valve to prevent blood pooling proximate the distal end of the conical shaped member 30.

As indicated above and also set forth in Applicant's U.S. Pat. Nos. 10,188,509 and 10,188,510, when the prosthetic valve 10c is engaged to a valve annulus; particularly, a mitral valve annulus, and receives fluid, i.e., blood, therein that exhibits a first positive fluid pressure, such as during late ventricular diastole/atrial systole, whereby a first positive pressure differential between first internal valvular pressure (resulting from the first positive fluid pressure) and first external pressure, i.e., left ventricle pressure, is generated, and, thereby, internal forces are exerted on the internal surface of the tissue valve 10c, i.e., sheet member 30, the sheet member 30 is adapted to expand (i.e., deflect outwardly) to an expanded configuration, as shown in phantom and denoted 30' in FIG. 6, and transition from the expanded configuration to a contracted configuration during transition of the first positive pressure differential to a second pressure differential between second internal valvular pressure and second external or left ventricle pressure, the second pressure differential being lower than the first positive pressure differential, such as when the blood within tissue valve 10c exhibits a second positive fluid pressure that is less than the first positive fluid pressure, i.e., a reduced positive fluid pressure, or a negative fluid pressure, whereby the forces exerted on the internal surface of the valve 10c, i.e., sheet member 30, decrease.

The interstices 36a-36d are preferably configured and adapted to open to an open or unrestricted configuration during the noted expansion of the conical shaped member 30' (denoted 36a', 36b', 36c' and 36d'), wherein the blood is allowed to be transmitted through the interstices 36a', 36b', 36c', 36d' and, hence, valve body, and into the left ventricle, and transition from the open or unrestricted configuration to a restricted or closed configuration during the noted transition of the sheet member 30 from the expanded configuration to the contracted configuration, wherein the blood through and out of the sheet member 30 is restricted, more preferably, abated.

As indicated above, in a preferred embodiment of the invention, the interstices 36a-36d are configured and adapted to transition from the restricted or closed configuration to a fully opened or unrestricted configuration when the second pressure differential between second internal valvular pressure and second external or left ventricle pressure is ≥10 mm Hg.

As indicated above, in a preferred embodiment of the invention, the total open area of the open interstices 36a', 36b', 36c', 36d' when the open interstices 36a', 36b', 36c', 36d' are in their fully opened configuration is at least 2× greater than the area of (or defined by) the open proximal annulus engagement end 32 of sheet member 30 and, hence, valve 10c.

As also indicated above, according to the invention, the prosthetic valve 10c (and similar "sheet structure" valves of the invention) can comprise an extracellular matrix (ECM) composition and/or a polymeric composition of the invention, and a collagenous mammalian tissue derived from a mammalian tissue source.

Referring now to FIGS. 7A and 7B, there are shown embodiments of prosthetic "ribbon structure" valves of the invention, where FIG. 7A illustrates one embodiment of a prosthetic "ribbon structure" valve having a tubular structure, denoted 10d, and FIG. 7B illustrates one embodiment of a prosthetic "ribbon structure" valve having a conical shaped structure, denoted 10e.

Asset forth in Applicant's U.S. Pat. Nos. 10,188,510 and 10,188,509, and U.S. application Ser. No. 16/129,968, which are incorporated by reference herein, prosthetic "ribbon structure" valve 10*d* is preferably employed to form prosthetic "ribbon structure" valve 10*d*.

As also set forth in Applicant's U.S. Pat. Nos. 10,188,510 and 10,188,509, and U.S. application Ser. No. 16/129,968 and illustrated in FIGS. 7A and 7B, the prosthetic "ribbon structure" valves 10*d*, 10*e* preferably comprise a base member 50 comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 7A and 7B, each of the plurality of ribbons 56 preferably comprise proximal and distal ends 56*a*, 56*b*, and first and second edge regions 53*a*, 53*b* that extend from the circumferential ribbon connection region 58 to the distal ends 56*b* of each of the ribbons 56 and, hence, distal end 54 of the base member 50.

As illustrated in FIG. 7B, the ribbons 56 of prosthetic "ribbon structure" valve 10*e* preferably taper to a substantially coincident point 55, wherein the base member 50 has a substantially conical shape.

As also illustrated in FIG. 7B, the distal ends 56*b* of the ribbons 56 of prosthetic "ribbon structure" valve 10*e* are preferably in a joined relationship, wherein blood flow through the joined distal ends 56*b* of the ribbons 56 is restricted.

As further illustrated in FIGS. 7A and 7B, the proximal ends 56*a* of ribbons 56 of prosthetic "ribbon structure" valves 10*d*, 10*e* are positioned circumferentially about the circumferential ribbon connection region 58 of the base member 50, wherein the first edge regions 53*a* and the second edge regions 53*b* of the ribbons 56 are positioned adjacent each other and form a plurality of fluid flow modulating regions 59.

According to the invention, the width of the circumferential ribbon connection region 58 can be increased or extended, whereby the length of ribbons 56 and, hence, flow modulating regions 59 can be adjusted to accommodate desired blood outflow from the prosthetic "ribbon structure" valves 10*d*, 10*e*.

As also indicated above and discussed in detail below, when the prosthetic "ribbon structure" valve 10*e* is engaged to a valve annulus; particularly, a mitral valve annulus, and receives blood flow therein that exhibits a positive fluid pressure gradient, internal forces are similarly exerted on the internal surface of the valve, 10*e*, i.e., taper region of base member 50 and, hence, ribbons 56.

As also indicated above and set forth in Applicant's U.S. Pat. Nos. 10,188,510 and 10,188,509, and application Ser. No. 16/129,968, when the prosthetic "ribbon structure" valve 10*e* is engaged to a valve annulus; particularly, a mitral valve annulus, and receives blood therein that exhibits a first positive fluid pressure, such as during late ventricular diastole/atrial systole, whereby there is similarly a first positive pressure differential between first internal valvular pressure (resulting from the first positive fluid pressure) and first external pressure, i.e., left ventricle pressure, and, hence, internal forces are similarly exerted on the internal surface of the valve 10*e*, i.e., taper region of base member 50, and, hence, flow modulating regions 59, the base member 50 is similarly adapted to expand to an expanded configuration, whereby the flow modulating regions 59 (i.e., ribbons 56) deflect outwardly to an open or unrestricted fluid flow configuration, as shown in phantom and denoted 50' in FIG. 7B, i.e., the first and second edge regions 53*a*, 53*b* separate, as shown in phantom and denoted 53*a*', 53*b*', whereby the blood is allowed to be transmitted through the flow modulating regions 59 and, hence, base member 50 of prosthetic "ribbon structure" valve 10*e*, and into the left ventricle.

The base member 50 and, hence, prosthetic "ribbon structure" valve 10*e* is similarly adapted to transition from the expanded configuration to a contracted configuration, whereby the ribbons 56 deflect inwardly and the flow modulating regions 59 transition from the open fluid flow configuration to a closed or restricted fluid flow configuration, during transition of the first positive pressure differential to a second pressure differential between second internal valvular pressure and second external or left ventricle pressure, the second pressure differential being lower than the first positive pressure differential, such as when blood within prosthetic "ribbon structure" valve 10*e* exhibits a second positive fluid pressure that is less than the first positive fluid pressure, i.e., a reduced positive fluid pressure, or a negative fluid pressure, wherein the blood through and out of the flow modulating regions 59 and, hence, base member 50 is restricted, more preferably, abated.

As indicated above, in a preferred embodiment of the invention, the flow modulating regions 59 of prosthetic "ribbon structure" valve 10*e* are similarly preferably configured and adapted to transition from the closed or restricted fluid flow configuration to a fully opened fluid flow configuration when the second pressure differential between second internal valvular pressure and second external or left ventricle pressure is ≥10 mm Hg.

In a preferred embodiment, the total area of the flow modulating regions 59' of prosthetic "ribbon structure" valve 10*e* when in the fully opened flow configurations is similarly at least 2× greater than the area of (or defined by) the open proximal annulus engagement end 52 of the base member and, hence, valve 10*d*.

Figure 7C:
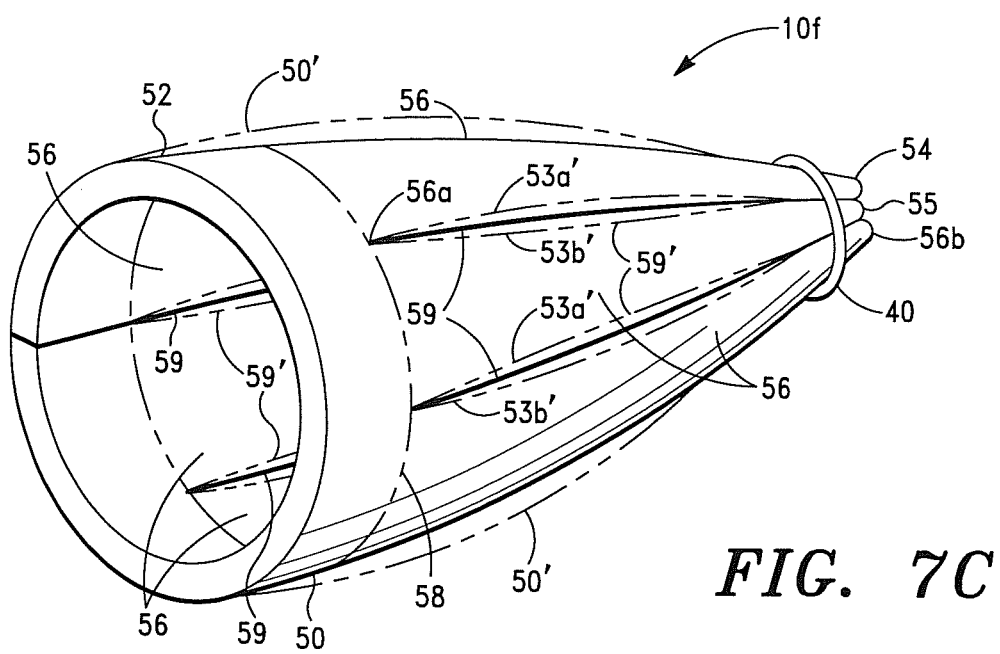
FIG. 7C is a perspective partial sectional view of another embodiment of the prosthetic "ribbon structure" valve shown in FIG. 7B having a structural ring disposed at the distal end of the valve, in accordance with the invention.

Referring now to FIG. 7C, there is shown another embodiment of the prosthetic "ribbon structure" valve 10*e* that is shown in FIG. 7B. As illustrated in FIG. 7C, the prosthetic valve, now denoted 10*f*, includes a support ring 40 that is disposed on the distal end 54 of the valve 10*f*.

According to the invention, the structural ring 40 is preferably sized and configured to receive ribbons 56 of prosthetic "ribbon structure" valve 10*f* therein in close proximity to each other, as shown in FIG. 7C.

Figure 8A:
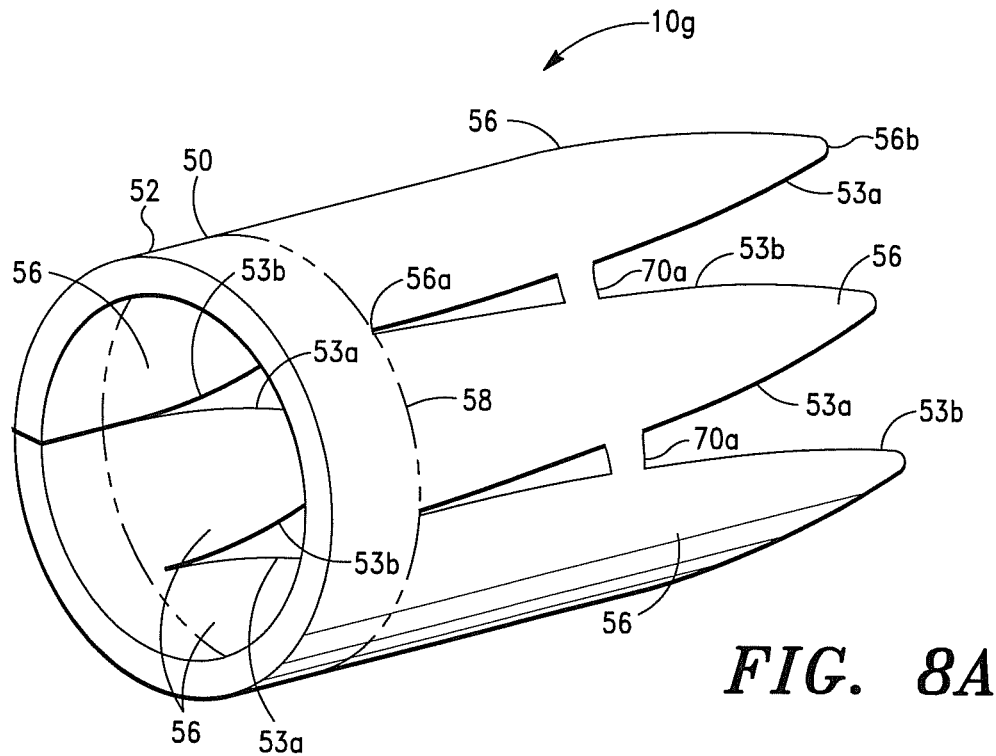
FIG. 8A is a perspective view of another embodiment of a prosthetic "ribbon structure" valve having an integral ribbon coupling member, in accordance with the invention.
Figure 8B:
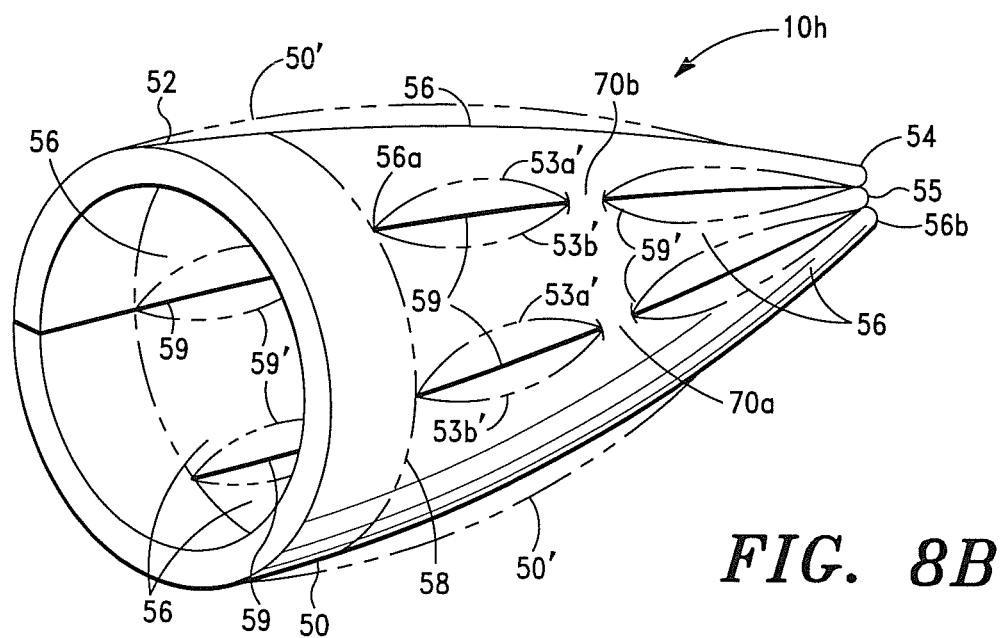
FIG. 8B is a perspective view of another embodiment of a prosthetic "ribbon structure" valve having an integral ribbon coupling member, in accordance with the invention.

Referring now to FIGS. 8A and 8B there are shown further embodiments of prosthetic "ribbon structure" valves, where FIG. 8A illustrates a prosthetic "ribbon structure" valve in a pre-operational configuration, denoted 10*g*, and FIG. 8B illustrates the prosthetic "ribbon structure" valve 10*g* in an operational configuration, denoted 10*h*.

As set forth in Applicant's Co-pending U.S. application Ser. No. 16/129,968, which is incorporated by reference herein, and illustrated in FIG. 8B, the prosthetic "ribbon structure" valve 10*h* also preferably comprises a base member 50 comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 8A and 8B, the prosthetic "ribbon structure" valve 10*h* further preferably comprises a plurality of constraining bands or coupling members 70*a*.

According to the invention, the coupling members 70*a* are sized and configured to couple (or join) a ribbon 56 to adjacent ribbons, i.e., couple a first edge region 53*a* of a first ribbon 56 to the second edge region 53b of a second ribbon 56, at a predetermined region.

According to the invention, the coupling members 70a can be disposed at any region between the proximal and distal ends 56a, 56b of the ribbons 56.

According to the invention, the coupling members 70a can comprise separate or integral members.

Figure 8C:
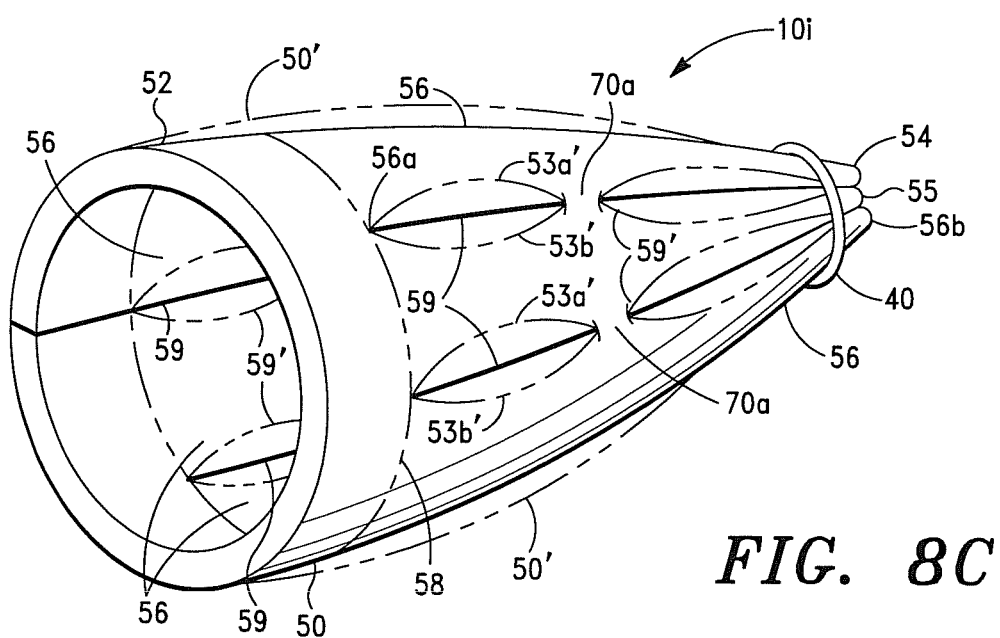
FIG. 8C is a perspective view of another embodiment the prosthetic "ribbon structure" valve shown in FIG. 8B having a support ring disposed at the distal end of the valve, in accordance with the invention.

Referring now to FIG. 8C, there is shown another embodiment of the prosthetic "ribbon structure" valve 10h that is shown in FIG. 8B. As illustrated in FIG. 8C, the prosthetic valve, now denoted 10i, similarly comprises a structural ring 40 that is disposed on the distal end 54 of the valve 10i.

In some embodiments of the invention, the prosthetic "ribbon structure" valves 10e-10i further comprise a supplemental support structure, such as described in Applicant's U.S. application Ser. No. 15/206,871, now U.S. Pat. No. 10,188,513, which is also incorporated by reference herein.

As indicated above, according to the invention, the "ribbon structure" valves 10e-10i (and similar "ribbon structure" valves of the invention) can similarly comprise an extracellular matrix (ECM) composition and/or a polymeric composition of the invention, and a collagenous mammalian tissue derived from a mammalian tissue source.

In a preferred embodiment of the invention, the prosthetic "ribbon structure" valves of the invention comprise crosslinked collagenous mammalian tissue, more preferably, crosslinked pericardium tissue that is processed via one of the aforementioned GA processing methods of the invention, wherein the GA processed crosslinked pericardium tissue exhibits a tensile strength in the range of in the range of 9.0 MPa to 12.0 MPa and an elastic phase slope, i.e., modulus (E), in the range of approximately 0.3 MPa to 0.5 MPa.

According to the invention, when the prosthetic "ribbon structure" conical shaped valves of the invention, i.e., valves 10e-10i, comprise the noted GA processed crosslinked pericardium tissue, the preferred conical region dimensions referenced above, fixed proximal and distal ends, and are subjected to an internal valvular pressure (Pit) of 10 mm Hg and 15 mm Hg during late ventricular diastole/early atrial systole and, hence, a pressure differential between the internal valvular pressure and ventricle pressure of approximately 10 mm Hg and 15 mm Hg ("$P_d$"), the prosthetic "ribbon structure" valves will exhibit the following seminal valve parameters and, hence, optimal valve function:

$P_d$=10 mmHg
  (i) $A_s$ (conical region)=27.8 cm$^2$
    (a) force exerted on internal surface of conical region: 3.71 N
    (b) deflection of ribbons @ mid-conical region (δ) where E=0.3 MPa: 8.40 mm
    (c) deflection of ribbons @ mid-conical region (δ) where E=0.5 MPa: 5.04 mm
  (ii) $A_s$ (conical region)=37.9 cm$^2$
    (a) force exerted on internal surface of conical region: 5.05 N
    (b) deflection of ribbons @ mid-conical region (δ) where E=0.3 MPa: 11.44 mm
    (c) deflection of ribbons @ mid-conical region (δ) where E=0.5 MPa: 6.86 mm $P_d$=15 mmHg
  (i) $A_s$ (conical region)=27.8 cm$^2$
    (a) force exerted on internal surface of conical region: 5.45 N
    (b) deflection of ribbons @ mid-conical region (δ) where E=0.3 MPa: 8.40 mm
    (c) deflection of ribbons @ mid-conical region (δ) where E=0.5 MPa: 5.04 mm
  (ii) $A_s$ (conical region)=37.9 cm$^2$
    (a) force exerted on internal surface of conical region: 7.43 N
    (b) deflection of ribbons @ mid-conical region (δ) where E=0.3 MPa: 12.27 mm
    (c) deflection of ribbons @ mid-conical region (δ) where E=0.5 MPa: 10.10 mm Referring now to FIGS. 9A and 10A, there are shown prosthetic "sheet structure" valve 10c and prosthetic "ribbon structure" valve 10f, respectively, engaged to mitral valve regions of a subject.

As illustrated in FIGS. 9A and 10A, in some embodiments of the invention, the prosthetic tissue valves of the invention, including the aforedescribed prosthetic "sheet structure" valve 10c and prosthetic "ribbon structure" valves 10e-10i, are solely engaged to the mitral valve annulus.

Figure 9B:
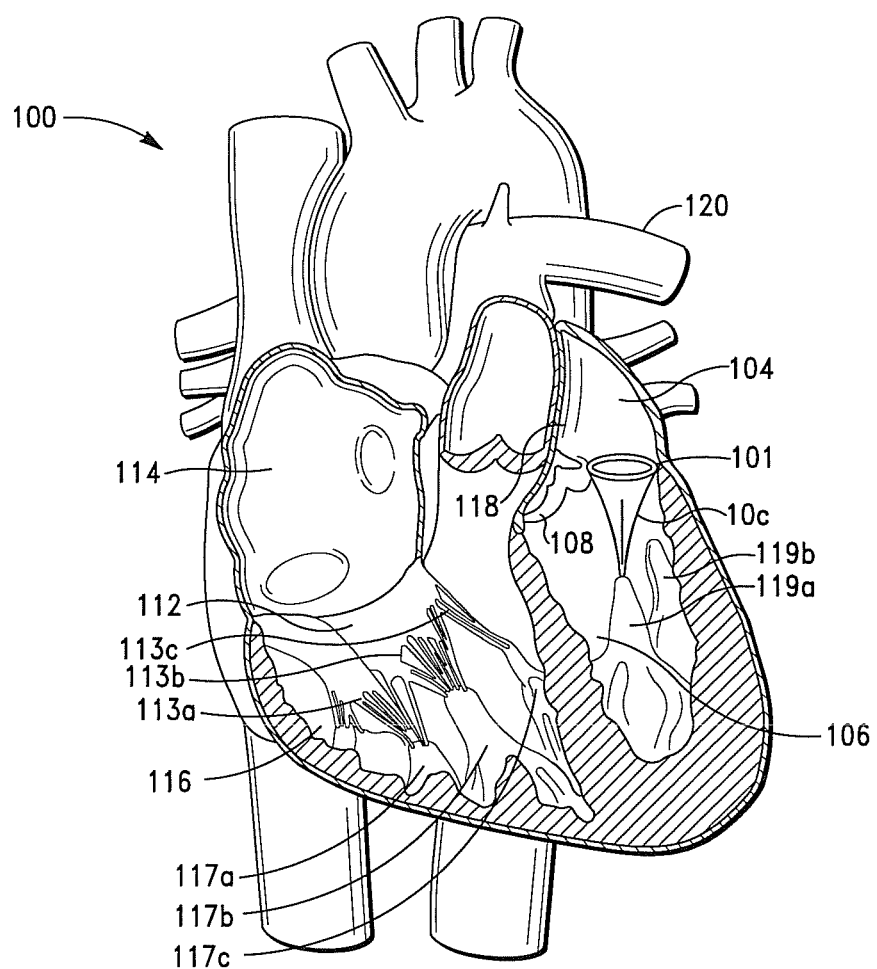
FIG. 9B is an illustration of the prosthetic "sheet structure" valve shown in FIG. 6 secured to a mitral valve annulus region and papillary muscle, in accordance with the invention.
Figure 10B:
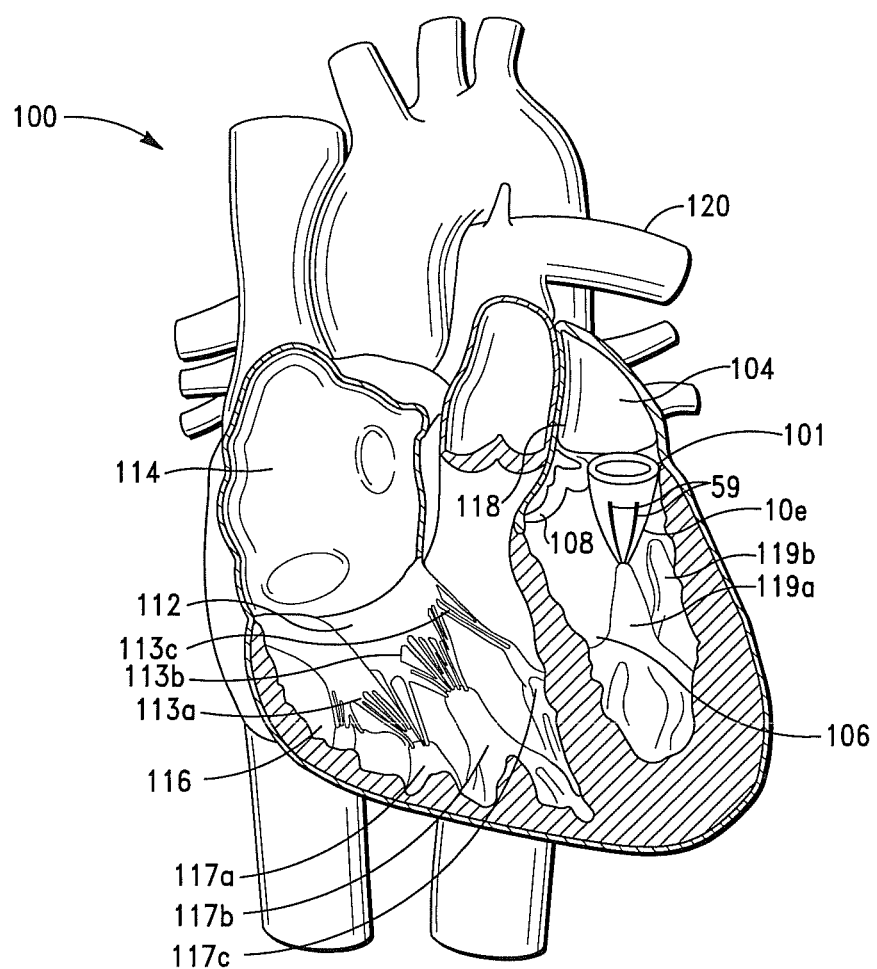
FIG. 10B is an illustration of the prosthetic "ribbon structure" valve shown in FIG. 7B secured to a mitral valve annulus region and papillary muscle, in accordance with the invention.

In some embodiments of the invention, the prosthetic valves of the invention, including the aforedescribed prosthetic "sheet structure" valve 10c and prosthetic "ribbon structure" valves 10e-10i, are engaged to a mitral valve annulus and to a papillary muscle, such as illustrated in FIGS. 9B and 10B, where prosthetic "sheet structure" valves 10c and 11e are engaged to the mitral valve annulus 101 and papillary muscle 119a.

According to the invention, the proximal cardiovascular engagement end of the prosthetic "sheet structure" and "ribbon structure" valves of the invention can be secured to a mitral valve annulus and the distal end disposed proximate to or engaged directly to a papillary muscle by any conventional method and means, e.g., suturing.

In a preferred embodiment of the invention, the prosthetic valves of the invention are implanted percutaneously, employing Applicant's proprietary percutaneous implantation methods disclosed in U.S. Pat. No. 10,857,263 and U.S. application Ser. Nos. 16/193,669 and 16/553,570.

According to the invention, when the proximal cardiovascular engagement end of a prosthetic valve of the invention is secured to a mitral valve annulus and the distal end of the valve is disposed proximate to or engaged directly to a papillary muscle, the prosthetic valve provides substantially increased prosthetic valve continuity from the mitral valve annulus to the left ventricle 106 compared to conventional prosthetic valves that are typically secured only to the mitral valve annulus.

In accordance with one embodiment of the invention there is thus provided a prosthetic valve for modulating fluid flow through a cardiovascular structure during cardiac cycles of a heart, comprising:

a base valve member comprising crosslinked pericardium tissue, the crosslinked pericardium tissue comprising an elastic phase slope (E) in the range of 0.3 MPa to 0.5 MPa, the base valve member further comprising an internal region, an open proximal valve member end and a distal valve member end, the open proximal valve member end being configured and adapted to engage an atrioventricular (AV) valve annulus, receive the fluid flow therein and direct first fluid of the fluid flow into the internal region of the base valve member, the open proximal valve member end defining an open valve inlet end comprising a first open area, the base valve member further comprising a plurality of elongated ribbon members that extend from the open proximal valve member end of the base valve member to the distal valve member end of the base valve member, each of the plurality of elongated ribbon members comprising first and second edge regions and proximal and distal ends, the plurality of elongated ribbon members being positioned circumferentially about the base valve member, wherein the first edge regions of the plurality of elongated ribbon members are positioned proximate the second edge regions of the plurality of elongated ribbon members and form a plurality of contiguous ribbon edge regions, the plurality of contiguous ribbon edge regions forming a plurality of flow modulating regions, the distal ends of the plurality of ribbon members being positioned proximate each other in a constrained relationship, wherein the base valve member comprises a conical shaped region and the fluid flow through the constrained distal ends of the plurality of elongated ribbon members is restricted, the plurality of elongated ribbon members being configured and adapted to deflect outwardly, whereby each of the plurality of flow modulating regions transitions from a restricted (or closed) fluid flow configuration to an open fluid flow configuration and allows the first fluid to be transmitted through and out of the base valve member when the base valve member is engaged to the AV valve annulus, the open proximal valve member end of the base valve member directs the first fluid into the internal region of the base valve member and the first fluid comprises a first positive fluid pressure, whereby a first positive pressure differential between first valvular pressure in the internal region of the base valve member relative to first external pressure exerted on the conical shaped region of the base valve member is generated, the plurality of elongated ribbon members being configured to outwardly deflect at least 8 mm when the first positive valve differential pressure is at least 10 MPa, the plurality of elongated ribbon members being further configured and adapted to deflect inwardly, whereby each of the flow modulating regions transitions from the open fluid flow configuration to the restricted fluid flow configuration and restricts the transmission of the first fluid through and out of the base valve member when the first positive pressure differential transitions to a second pressure differential between second valvular pressure in the internal region of the base valve member relative to second external pressure exerted on the conical shaped region of the base valve member, the second pressure differential being lower than the first positive pressure differential.

In another embodiment of the invention, there is provided a method for replacing a defective heart valve with a prosthetic valve of the invention, comprising the steps of:

(i) providing a prosthetic valve comprising a base valve member, the base valve member comprising cross-linked pericardium tissue, the crosslinked pericardium tissue comprising an elastic phase slope (E) in the range of 0.3 MPa to 0.5 MPa, the base valve member further comprising an internal region, an open proximal valve member end and a distal valve member end, the open proximal valve member end being configured and adapted to engage an atrioventricular (AV) valve annulus, receive the fluid flow therein and direct first fluid of the fluid flow into the internal region of the base valve member, the open proximal valve member end defining an open valve inlet end comprising a first open area, the base valve member further comprising a plurality of elongated ribbon members that extend from the open proximal valve member end of the base valve member to the distal valve member end of the base valve member, each of the plurality of elongated ribbon members comprising first and second edge regions and proximal and distal ends, the plurality of elongated ribbon members being positioned circumferentially about the base valve member, wherein the first edge regions of the plurality of elongated ribbon members are positioned proximate the second edge regions of the plurality of elongated ribbon members and form a plurality of contiguous ribbon edge regions, the plurality of contiguous ribbon edge regions forming a plurality of flow modulating regions, the distal ends of the plurality of ribbon members being positioned proximate each other in a constrained relationship, wherein the base valve member comprises a conical shaped region and the fluid flow through the constrained distal ends of the plurality of elongated ribbon members is restricted, the plurality of elongated ribbon members being configured and adapted to deflect outwardly, whereby each of the plurality of flow modulating regions transitions from a restricted (or closed) fluid flow configuration to an open fluid flow configuration and allows the first fluid to be transmitted through and out of the base valve member when the base valve member is engaged to the AV valve annulus, the open proximal valve member end of the base valve member directs the first fluid into the internal region of the base valve member and the first fluid comprises a first positive fluid pressure, whereby a first positive pressure differential between first valvular pressure in the internal region of the base valve member relative to first external pressure exerted on the conical shaped region of the base valve member is generated, the plurality of elongated ribbon members being further configured and adapted to deflect inwardly, whereby each of the flow modulating regions transitions from the open fluid flow configuration to the restricted fluid flow configuration and restricts the transmission of the first fluid through and out of the base valve member when the first positive pressure differential transitions to a second pressure differential between second valvular pressure in the internal region of the base valve member relative to second external pressure exerted on the conical shaped region of the base valve member, the second pressure differential being lower than the first positive pressure differential;

(ii) providing a catheter assembly adapted to access to a valve annulus region of a heart, the catheter assembly comprising a portal catheter, catheter guide, anchor insertion device, anchor guidewire, anchor, valve insertion device and valve securing device, the portal catheter comprising a catheter portal sheath comprising proximal and distal ends and an access portal therein that is sized and configured to receive and route therethrough the catheter guide, the anchor insertion device, the anchor guidewire, the anchor, the valve insertion device and the valve securing device, the portal catheter further comprising a catheter control assembly adapted to control the portal catheter and, thereby the catheter guide, the anchor insertion device, the anchor guidewire, the anchor, the valve insertion device and the valve securing device when disposed therein, the catheter guide comprising a guide head and a guide shaft having an internal guide lumen therein that is sized and configure to receive a first guidewire therein, the guide head being configured to pierce through biological tissue, the anchor insertion device comprising an elongated member having an internal anchor insertion device lumen therein that is sized and configured to receive the anchor guidewire and anchor therein, the anchor insertion device further comprising an actuation mechanism adapted to control the elongated member, the anchor guidewire and anchor when disposed therein, the anchor guidewire comprising anchor guidewire proximal and distal ends, the anchor being disposed on the anchor guidewire distal end, the anchor being configured to engage cardiovascular tissue, the valve insertion device comprising a valve insertion member and a base member comprising proximal and distal ends and a base member internal lumen therein that is adapted to receive pressurized air therein, the valve insertion device further comprising an expandable member disposed on the distal end of the base member, the expandable member being adapted to transition from a pre-deployment configuration to and expanded post-deployment configuration, the valve securing device comprising a securing shaft comprising a proximal end and a multi-function distal end that is adapted to position the anchor in the cardiovascular tissue, engage the closed distal end region of the prosthetic valve and sever a guidewire, the valve securing device further comprising at least one valve securing device actuation mechanism that is adapted to control the multi-function distal end;

(iii) preparing a first catheter sub-assembly comprising the portal catheter, the catheter guide and the first guidewire;

(iv) selecting a vein in communication with a subject's heart, the vein providing access to an AV valve annulus region of the subject's heart;

(v) placing an incision through tissue proximate the vein and through the vein, wherein an opening is provided in the vein;

(vi) inserting the first catheter sub-assembly through the incision and into and through the vein, and into the right atrium of the subject's heart;

(vii) advancing the first catheter sub-assembly into the left atrium of the subject's heart;

(viii) retracting the catheter guide and the first guidewire through the access portal of the catheter portal sheath and out of the subject's body;

(ix) inserting the anchor insertion device and the anchor guidewire into the access portal of the catheter portal sheath;

(x) routing the anchor insertion device through the access portal of the catheter portal sheath and into a left ventricle of the subject's heart;

(xi) positioning the anchor of the anchor guidewire at a predetermined anchor attachment point between anterior and posterior papillary muscles;

(xii) attaching the anchor to a myocardium of the subject's heart at the predetermined anchor attachment point;

(xiii) withdrawing the anchor insertion device through the access portal of the catheter portal sheath, wherein the anchor and the anchor guidewire remain connected to the myocardium;

(xiv) securing the open proximal valve member end of the base valve member to an expandable proximal guide ring, the expandable proximal guide ring being adapted to transition from a guide ring pre-deployment configuration to a guide ring expanded post-deployment configuration;

(xv) positioning the base valve member of the prosthetic valve on the expandable member of the valve insertion device;

(xvi) routing the anchor guidewire into and through the closed base valve member distal end;

(xvii) inserting the valve insertion device with the base valve member engaged thereto into and through the access portal of the catheter portal sheath along the anchor guidewire and into the AV valve annulus region of the subject's heart;

(xviii) positioning base valve member proximate the AV valve annulus;

(xix) expanding the expandable member of the valve insertion device, wherein the expandable member expands to the expanded post-deployment configuration and, thereby, the base valve member of the prosthetic valve expands to the expanded configuration and the expandable proximal guide ring expands to the guide ring expanded post-deployment configuration, whereby the base valve member is disposed adjacent the AV valve annulus;

(xx) retracting the valve insertion device through the access portal of the catheter portal sheath and out of the subject's body;

(xxi) inserting the valve securing device into and through the access portal of the catheter portal sheath, and into the internal region of the base valve member of the prosthetic valve;

(xxii) ensnaring the closed base valve member distal end of the base valve member with the multi-function distal end of the valve securing device;

(xxiii) connecting the closed base valve member distal end to the anchor, whereby the prosthetic valve is engaged to the myocardium;

(xxiv) positioning the multi-function distal end of the valve securing device at a predetermined anchor guidewire severing point proximate the anchor;

(xxv) severing the anchor guidewire at the predetermined anchor guidewire severing point with the valve securing device;

(xxvi) withdrawing the valve securing device and the severed anchor guidewire through the access portal of the catheter portal sheath;

(xxvii) inserting a suturing device into and through the access portal of the catheter portal sheath to the open proximal valve member end of the base valve member;

(xxviii) suturing the open proximal valve member end of the base valve member to the AV valve annulus; and (xxix) withdrawing the catheter portal sheath out of the left atrium of the subject's heart and out of the subject's body.

In another embodiment of the invention there is provided a prosthetic valve for modulating fluid flow through a cardiovascular structure during cardiac cycles of a heart, comprising:

a base valve member comprising a conical shape, the base valve member further comprising crosslinked pericardium tissue, the crosslinked pericardium tissue comprising an elastic phase slope (E) in the range of 0.3 MPa to 0.5 MPa, the base valve member further comprising an internal region, an exterior region, an open proximal valve member end and a closed distal valve member end, the open proximal valve member end being configured and adapted to engage an atrioventricular (AV) valve annulus, receive the fluid flow therein and direct first fluid of the fluid flow into the internal region of the base valve member, the open proximal valve member end defining an open valve inlet end comprising a first open area, the base valve member further comprising a plurality of linear interstices disposed between the open proximal valve member end and the closed distal valve member end, the plurality of linear interstices not extending to the closed distal valve member end, the base valve member, when engaged to the AV valve annulus, being configured and adapted to expand and transition from a contracted configuration to an expanded configuration when the open proximal valve member end of the base valve member directs the first fluid into the internal region of the base valve member, and the first fluid comprises a first positive fluid pressure, whereby a first positive pressure differential between first valvular pressure in the internal region of the base valve member relative to first external pressure exerted on the exterior region of the base valve member is generated, the plurality of linear interstices being configured and adapted to transition from a restricted fluid flow configuration to an unrestricted fluid flow configuration, wherein the plurality of linear interstices allows the first fluid to be transmitted through and out of the base valve member, when the base valve member expands and transitions from the contracted configuration to the expanded configuration, the plurality of plurality of linear interstices being further configured and adapted to transition to a fully unrestricted flow configuration when the first positive valve differential pressure is at least 10 MPa, the base valve member being further configured and adapted to transition from the expanded configuration to the contracted configuration when the first positive pressure differential transitions to a second pressure differential between second valvular pressure in the internal region of the base valve member relative to second external pressure exerted on the exterior region of the base valve member, the second pressure differential being lower than the first positive pressure differential, the plurality of linear interstices being further configured and adapted to transition from the unrestricted fluid flow configuration to the restricted fluid flow configuration, wherein the plurality of linear interstices restricts the transmission of the first fluid through and out of the base valve member, when the base valve member transitions from the expanded configuration to the contracted configuration.

As indicated above, according to the invention, the reduced second valve differential pressure can result from a reduced pressure of the fluid transmitted into the internal region of the base valve member and, thereby, reduced valvular pressure in the internal region of the base valve member, and/or reduced exterior pressure, such as left ventricle pressure when the AV valve annulus comprises a mitral valve annulus.

As indicated above and will readily be appreciated by one having ordinary skill in the art, the present invention provides numerous advantages compared to prior art prosthetic heart valves. Among the advantages are the following:

The provision of prosthetic valves; particularly, prosthetic mitral valves, which provide optimum blood flow modulation and characteristics.

The provision of prosthetic valves; particularly, prosthetic mitral valves, which comprise an optimal sheet structure, including (i) an increased flow modulation means (i.e., leaflet) coaptation surface area compared to conventional prosthetic valve structures, which minimizes fluid; more specifically, blood flow turbulence within the valve body, and (ii) an increased flow modulation means coaptation length compared to conventional prosthetic valve structures, which decreases the likelihood of regurgitation during ventricular systole.

The provision of prosthetic valves; particularly, prosthetic mitral valves, which are fully functional without a support structure, e.g., stent frame, and, hence, do not comprise a support structure, which can, and in many instances will, disrupt blood flow through the outflow tract.

The provision of prosthetic valves; particularly, prosthetic mitral valves, which comprise a plurality of "independent" flow modulation means, whereby, if one flow modulation means is defective or fails, valve function is minimally disrupted, if at all.

The provision of prosthetic valves; particularly, prosthetic mitral valves, which are configured and adapted to provide a maximum blood flow rate across a mitral valve annulus region that is at least equivalent to, and, in some instances, greater than, the maximum blood flow rate across a mitral valve annulus region with a native mitral valve for a given period of time during a cardiac cycle.

The provision of prosthetic valves; particularly, prosthetic mitral valves, which are further configured and adapted to provide a blood flow rate into the left ventricle during atrial systole that is at least equivalent to, and, in some instances, greater than, the blood flow into the left ventricle during atrial systole with a native mitral valve.

The provision of prosthetic valves; particularly, prosthetic mitral valves, which are further configured and adapted to provide optimal blood flow characteristics of blood directed into the left ventricle and, thereby, optimal vortex dynamics inside the left ventricle.

The provision of prosthetic valves; particularly, prosthetic mitral valves, which comprise a structure and configuration that substantially reduces disruption of blood flow out of the left ventricle and into and, hence, through the aortic valve, when implanted in a patient.

The provision of prosthetic valves; particularly, prosthetic mitral valves, which are further configured and adapted to provide a pressure half-time (PHT) that is at least equivalent to the PHT of a normal native mitral valve, i.e., the time interval in milliseconds between the maximum mitral gradient during ventricular diastole and the time point where the mitral gradient is half the maximum initial value.

The provision of prosthetic valves; particularly, prosthetic mitral valves, which can be disposed in a mitral valve annulus and over native mitral valves without resection of the native leaflets or fixing the leaflets in an open configuration, which will allow the native leaflets to normally close during ventricular systole.

The provision of prosthetic valves; particularly, prosthetic mitral valves, comprising collagenous mammalian tissue with minimal in vivo calcification and cytotoxicity.

The provision of prosthetic valves; particularly, prosthetic mitral valves, comprising collagenous mammalian tissue devoid of devoid of xenogeneic antigens, which can, and often will, induce adverse immune responses in vivo.

The provision of prosthetic valves; particularly, prosthetic mitral valves, which are adapted to deliver biologically active agents, such as growth factors, and pharmacological agents, such as anti-inflammatories, to cardiovascular tissue, when disposed proximate thereto.

The provision of methods for replacing diseased or defective native heart valves with improved prosthetic xenograft valves.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve for modulating fluid flow through a cardiovascular structure during cardiac cycles of a heart, comprising:

a base valve member comprising crosslinked mammalian collagenous tissue, said crosslinked mammalian collagenous tissue comprising crosslinked pericardium tissue, said crosslinked pericardium tissue comprising an elastic phase slope (E) in the range of 0.3 MPa to 0.5 MPa, said base valve member further comprising an internal region, an open proximal valve member end and a distal valve member end, said open proximal valve member end being configured and adapted to engage an atrioventricular (AV) valve annulus, receive said fluid flow therein and direct first fluid of said fluid flow into said internal region of said base valve member, said open proximal valve member end defining an open valve inlet end comprising a first open area, said base valve member further comprising a plurality of elongated ribbon members that extend from said open proximal valve member end of said base valve member to said distal valve member end of said base valve member, each of said plurality of elongated ribbon members comprising first and second edge regions and proximal and distal ends, said plurality of elongated ribbon members being positioned circumferentially about said base valve member, wherein said first edge regions of said plurality of elongated ribbon members are positioned proximate said second edge regions of said plurality of elongated ribbon members and form a plurality of contiguous ribbon edge regions, said plurality of contiguous ribbon edge regions forming a plurality of flow modulating regions, said distal ends of said plurality of elongated ribbon members being positioned proximate each other in a constrained relationship, wherein said base valve member comprises a conical shaped region and said fluid flow through said distal ends of said plurality of elongated ribbon members is restricted, said plurality of elongated ribbon members being configured and adapted to deflect outwardly, whereby each of said plurality of flow modulating regions transitions from a restricted fluid flow configuration to an open fluid flow configuration and allows said first fluid to be transmitted through and out of said base valve member, when said base valve member is engaged to said AV valve annulus, said open proximal valve member end of said base valve member directs said first fluid into said internal region of said base valve member and said first fluid comprises a first positive fluid pressure, whereby a first positive pressure differential between first valvular pressure in said internal region of said base valve member relative to first external pressure exerted on said conical shaped region of said base valve member is generated, said plurality of elongated ribbon members being further configured and adapted to deflect inwardly, whereby each of said plurality of flow modulating regions transitions from said open fluid flow configuration to said restricted fluid flow configuration and restricts said transmission of said first fluid through and out of said base valve member when said first positive pressure differential transitions to a second pressure differential between second valvular pressure in said internal region of said base valve member relative to second external pressure exerted on said conical shaped region of said base valve member, said second pressure differential being lower than said first positive pressure differential.

2. The prosthetic valve of claim 1, wherein said crosslinked pericardium tissue comprises a tensile strength in the range of 9 MPa to 12 MPa.

3. The prosthetic valve of claim 1, wherein said plurality of flow modulating regions in said open fluid flow configuration define a fluid outlet area of said base valve member, said fluid outlet area of said base valve member being at least two times greater than said first open area of said open valve inlet end.

4. The prosthetic valve of claim 1, wherein said crosslinked pericardium tissue comprises crosslinked bovine pericardium tissue.

5. The prosthetic valve of claim 1, wherein said crosslinked pericardium tissue comprises a pharmacological agent.

6. The prosthetic valve of claim 5, wherein said pharmacological agent comprises a pharmacological agent selected from the group consisting of desoximetasone, sirolimus, cyclosporine and prednisolone.

7. The prosthetic valve of claim 5, wherein said pharmacological agent comprises a HMG-CoA reductase inhibitor selected from the group consisting of atorvastatin, cerivastatin, fluvastatin and lovastatin.

8. The prosthetic valve of claim 1, wherein said crosslinked pericardium tissue is derived from pericardium tissue devoid of xenogeneic antigens.

* * * * *